(12) United States Patent
Jang

(10) Patent No.: US 9,078,778 B2
(45) Date of Patent: Jul. 14, 2015

(54) INTRAVASCULAR STENT

(75) Inventor: G. David Jang, Redlands, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 512 days.

(21) Appl. No.: 13/232,640

(22) Filed: Sep. 14, 2011

(65) Prior Publication Data
US 2012/0065724 A1    Mar. 15, 2012

Related U.S. Application Data

(63) Continuation of application No. 10/206,432, filed on Jul. 25, 2002, now Pat. No. 8,021,414, which is a continuation of application No. 09/574,077, filed on May 18, 2000, now Pat. No. 6,770,088, which is a (Continued)

(51) Int. Cl.
*A61F 2/82* (2013.01)
*A61F 2/915* (2013.01)
(Continued)

(52) U.S. Cl.
CPC . *A61F 2/915* (2013.01); *A61F 2/91* (2013.01); *A61F 2/958* (2013.01); *A61F 2002/91525* (2013.01); *A61F 2002/91533* (2013.01); *A61F 2002/91558* (2013.01); *A61F 2230/0054* (2013.01); *A61F 2250/0018* (2013.01)

(58) Field of Classification Search
CPC .............. A61F 2/89; A61F 2/91; A61F 2/915
USPC ................................................. 623/1.15, 1.16
See application file for complete search history.

(56) References Cited

U.S. PATENT DOCUMENTS 2,836,181 A    5/1958  Tapp
3,105,492 A   10/1963  Jeckel
3,272,204 A    9/1966  Artandi et al.
(Continued)

FOREIGN PATENT DOCUMENTS

DE    4303181       8/1994
DE    4303181 A1    8/1994
(Continued)

OTHER PUBLICATIONS

Russ Olexa, "Keepin Accuracy Within Reach", MMS Online, Gardner Publications, Inc.
(Continued)

*Primary Examiner* — Randy Shay
*Assistant Examiner* — Dinah Baria
(74) *Attorney, Agent, or Firm* — Vidas, Arrett & Steinkraus, P.A.

(57) ABSTRACT

A stent in a non-expanded state has a first and second expansion column, each consisting of a plurality of expansion strut pairs. An expansion strut pair includes a first expansion strut, a second expansion strut and a joining strut that couples the first and second expansion struts at one end. A connecting strut column, formed of a plurality of connecting struts couples the first and second expansion columns. Connecting struts include a proximal section, a distal section and an intermediate section. The proximal section is coupled to the corner of an expansion strut pair of the first expansion column, and the distal section is coupled to the joining strut of an expansion strut pair of the second expansion column intermediate the expansion strut pair first corner and the expansion strut pair second corner.

12 Claims, 29 Drawing Sheets

Related U.S. Application Data continuation-in-part of application No. 08/845,657, filed on Apr. 25, 1997, now Pat. No. 5,922,021, which is a continuation of application No. 08/845,734, filed on Apr. 25, 1997, now abandoned, which is a continuation-in-part of application No. 08/824,865, filed on Mar. 26, 1997, now Pat. No. 6,152,957, which is a continuation-in-part of application No. 08/824,866, filed on Mar. 26, 1997, now Pat. No. 5,954,743, which is a continuation-in-part of application No. 08/824,142, filed on Mar. 25, 1997, now Pat. No. 6,241,760.

(60) Provisional application No. 60/017,484, filed on Apr. 26, 1996.

(51) Int. Cl.
  A61F 2/91 (2013.01)
  A61F 2/958 (2013.01)

(56) References Cited

U.S. PATENT DOCUMENTS

| | | | |
|---|---|---|---|
| 3,490,975 | A | 1/1970 | Lightwood et al. |
| 3,509,883 | A | 5/1970 | Dibelius |
| 3,526,228 | A | 9/1970 | Lyng |
| 3,562,820 | A | 2/1971 | Braun |
| 3,635,215 | A | 1/1972 | Shea et al. |
| 3,771,526 | A | 11/1973 | Rudle |
| 3,868,956 | A | 3/1975 | Alfidi et al. |
| 3,993,078 | A | 11/1976 | Bergentz et al. |
| 4,078,167 | A | 3/1978 | Banas |
| 4,127,761 | A | 11/1978 | Pauley |
| 4,130,904 | A | 12/1978 | Whalen |
| 4,140,126 | A | 2/1979 | Choudhury |
| 4,141,364 | A | 2/1979 | Schultze |
| 4,164,045 | A | 8/1979 | Bokros |
| 4,214,587 | A | 7/1980 | Sakura, Jr. |
| 4,300,244 | A | 11/1981 | Bokros |
| 4,313,231 | A | 2/1982 | Koyamada |
| 4,319,363 | A | 3/1982 | Ketharanathan |
| 4,425,908 | A | 1/1984 | Simon |
| 4,441,215 | A | 4/1984 | Kaster |
| 4,470,407 | A | 9/1984 | Hussein |
| 4,501,264 | A | 2/1985 | Rockey |
| 4,503,569 | A | 3/1985 | Dotter |
| 4,512,338 | A | 4/1985 | Balko |
| 4,535,770 | A | 8/1985 | Lemole |
| 4,550,447 | A | 11/1985 | Seiler, Jr. |
| 4,553,545 | A | 11/1985 | Maass |
| 4,560,374 | A | 12/1985 | Hammerslag |
| 4,580,568 | A | 4/1986 | Gianturco |
| 4,597,389 | A | 7/1986 | Ibrahim |
| 4,647,416 | A | 3/1987 | Seiler, Jr. |
| 4,649,922 | A | 3/1987 | Wiktor |
| 4,655,771 | A | 4/1987 | Wallsten |
| 4,655,776 | A | 4/1987 | Lesinski |
| 4,665,918 | A | 5/1987 | Garza |
| 4,681,110 | A | 7/1987 | Wiktor |
| 4,693,721 | A | 9/1987 | Ducheyne |
| 4,733,665 | A | 3/1988 | Palmaz |
| 4,739,762 | A | 4/1988 | Palmaz |
| 4,740,207 | A | 4/1988 | Kreamer |
| 4,760,849 | A | 8/1988 | Kropf |
| 4,762,128 | A | 8/1988 | Rosenbluth |
| 4,768,507 | A | 9/1988 | Fischell et al. |
| 4,769,029 | A | 9/1988 | Patel |
| 4,771,773 | A | 9/1988 | Kropf |
| 4,776,337 | A | 10/1988 | Palmaz |
| 4,787,899 | A | 11/1988 | Lazarus |
| 4,795,458 | A | 1/1989 | Regan |
| 4,795,465 | A | 1/1989 | Marten |
| 4,800,882 | A | 1/1989 | Gianturco |
| 4,820,298 | A | 4/1989 | Leveen |
| 4,830,003 | A | 5/1989 | Wolff |
| 4,842,575 | A | 6/1989 | Hoffman, Jr. |
| 4,848,343 | A | 7/1989 | Wallsten |
| 4,851,009 | A | 7/1989 | Pinchuk |
| 4,856,516 | A | 8/1989 | Hillstead |
| 4,872,874 | A | 10/1989 | Taheri |
| 4,877,030 | A | 10/1989 | Beck |
| 4,878,906 | A | 11/1989 | Lindemann et al. |
| 4,886,062 | A | 12/1989 | Wiktor |
| 4,913,141 | A | 4/1990 | Hillstead |
| 4,922,905 | A | 5/1990 | Strecker |
| 4,950,227 | A | 8/1990 | Savin |
| 4,950,258 | A | 8/1990 | Kawai |
| 4,994,071 | A | 2/1991 | MacGregor |
| 5,015,253 | A | 5/1991 | MacGregor |
| 5,019,090 | A | 5/1991 | Pinchuk |
| 5,035,706 | A | 7/1991 | Giantureo |
| 5,037,392 | A | 8/1991 | Hillstead |
| 5,059,211 | A | 10/1991 | Stack |
| 5,064,435 | A | 11/1991 | Porter |
| 5,092,877 | A | 3/1992 | Pinchuk |
| 5,102,417 | A | 4/1992 | Palmaz |
| 5,104,399 | A | 4/1992 | Lazarus |
| 5,104,404 | A * | 4/1992 | Wolff .................. 623/1.16 |
| 5,108,417 | A | 4/1992 | Sawyer |
| 5,122,154 | A | 6/1992 | Rhodes |
| 5,133,732 | A | 7/1992 | Wiktor |
| 5,135,536 | A | 8/1992 | Hillstead |
| 5,139,480 | A | 8/1992 | Hickle |
| 5,147,385 | A | 9/1992 | Beck |
| 5,147,400 | A | 9/1992 | Kaplan |
| 5,158,548 | A | 10/1992 | Lau |
| 5,163,952 | A | 11/1992 | Froix |
| 5,192,289 | A | 3/1993 | Jessen |
| 5,195,984 | A | 3/1993 | Schatz |
| 5,197,978 | A | 3/1993 | Hess |
| 5,217,483 | A | 6/1993 | Tower |
| 5,226,913 | A | 7/1993 | Pinchuk |
| 5,269,802 | A | 12/1993 | Garber |
| 5,282,823 | A | 2/1994 | Schwartz |
| 5,282,824 | A | 2/1994 | Gianturco |
| 5,292,331 | A | 3/1994 | Boneau |
| 5,304,200 | A | 4/1994 | Spaulding |
| 5,312,430 | A | 5/1994 | Rosenbluth |
| 5,314,472 | A | 5/1994 | Fontaine |
| 5,344,425 | A | 9/1994 | Sawyer |
| 5,354,263 | A | 10/1994 | Coll |
| 5,354,308 | A | 10/1994 | Simon et al. |
| 5,360,443 | A | 11/1994 | Barone |
| 5,383,892 | A | 1/1995 | Cardon et al. |
| 5,389,106 | A | 2/1995 | Tower |
| 5,405,377 | A | 4/1995 | Cragg |
| 5,421,955 | A | 6/1995 | Lau |
| 5,449,373 | A * | 9/1995 | Pinchasik et al. ............ 606/198 |
| 5,507,767 | A | 4/1996 | Maeda et al. |
| 5,527,354 | A | 6/1996 | Fontaine |
| 5,540,712 | A * | 7/1996 | Kleshinski et al. .......... 623/1.19 |
| 5,545,210 | A | 8/1996 | Hess |
| 5,549,663 | A | 8/1996 | Cottone, Jr. |
| 5,575,818 | A | 11/1996 | Pinchuk |
| 5,591,197 | A * | 1/1997 | Orth et al. ................. 623/1.16 |
| 5,591,229 | A | 1/1997 | Parodi |
| 5,593,442 | A | 1/1997 | Klein |
| 5,601,593 | A | 2/1997 | Freitag |
| 5,607,442 | A | 3/1997 | Fischell |
| 5,607,444 | A | 3/1997 | Lam |
| 5,609,627 | A | 3/1997 | Goicoechea et al. |
| 5,613,981 | A | 3/1997 | Boyle et al. |
| 5,617,878 | A | 4/1997 | Taheri |
| 5,618,301 | A | 4/1997 | Hauenstein |
| 5,653,727 | A | 8/1997 | Wiktor |
| 5,669,924 | A | 9/1997 | Shaknovich |
| 5,676,671 | A | 10/1997 | Inoue |
| 5,676,696 | A | 10/1997 | Marcade |
| 5,693,086 | A | 12/1997 | Goicoechea et al. |
| 5,695,516 | A | 12/1997 | Fischell et al. |
| 5,697,971 | A | 12/1997 | Fischell et al. |
| 5,707,386 | A | 1/1998 | Schnepp-Pesch |
| 5,713,949 | A | 2/1998 | Jayaraman |
| 5,716,393 | A | 2/1998 | Lindenberg |

(56) References Cited

U.S. PATENT DOCUMENTS

| | | |
|---|---|---|
| 5,718,713 A | 2/1998 | Frantzen |
| 5,733,301 A | 3/1998 | Forman |
| 5,733,303 A * | 3/1998 | Israel et al. ............ 623/1.15 |
| 5,735,871 A | 4/1998 | Sgro |
| 5,735,893 A | 4/1998 | Lau et al. |
| 5,741,327 A | 4/1998 | Frantzen |
| 5,755,771 A | 5/1998 | Penn et al. |
| 5,755,776 A | 5/1998 | Al-Saadon |
| 5,755,781 A | 5/1998 | Jayaraman |
| 5,759,192 A | 6/1998 | Saunders |
| 5,772,864 A | 6/1998 | Moller |
| 5,776,161 A | 7/1998 | Globerman |
| 5,776,181 A | 7/1998 | Lee |
| 5,776,183 A | 7/1998 | Kanesaka |
| 5,782,906 A | 7/1998 | Marshall et al. |
| 5,807,404 A | 9/1998 | Richter |
| 5,810,067 A | 9/1998 | Atari |
| 5,810,767 A | 9/1998 | Klein |
| 5,810,872 A | 9/1998 | Kanesaka |
| 5,824,043 A | 10/1998 | Cottone, Jr. |
| 5,824,059 A | 10/1998 | Wijay |
| 5,827,321 A | 10/1998 | Roubin et al. |
| 5,836,951 A | 11/1998 | Rosenbluth |
| 5,836,964 A | 11/1998 | Richter |
| 5,843,117 A | 12/1998 | Alt |
| 5,843,120 A | 12/1998 | Israel |
| 5,843,172 A | 12/1998 | Yan |
| 5,853,419 A | 12/1998 | Imran |
| 5,860,999 A | 1/1999 | Schnepp-Pesch |
| 5,861,027 A | 1/1999 | Trapp |
| 5,876,449 A | 3/1999 | Starck |
| 5,879,370 A | 3/1999 | Fischell |
| 5,895,406 A | 4/1999 | Gray |
| 5,897,588 A | 4/1999 | Hull et al. |
| 5,902,317 A | 5/1999 | Kleshinski |
| 5,902,332 A | 5/1999 | Schatz |
| 5,907,893 A | 6/1999 | Zadno-Azizi et al. |
| 5,911,754 A | 6/1999 | Kanesaka |
| 5,913,895 A | 6/1999 | Burpee et al. |
| 5,922,019 A | 7/1999 | Hankh |
| 5,922,020 A | 7/1999 | Klein et al. |
| 5,922,021 A | 7/1999 | Jang |
| 5,938,682 A | 8/1999 | Hojeibane et al. |
| 5,938,697 A | 8/1999 | Killion et al. |
| 5,939,227 A | 8/1999 | Smith |
| 5,948,016 A | 9/1999 | Jang |
| 5,953,743 A | 9/1999 | Jeddeloh |
| 5,954,743 A | 9/1999 | Jang |
| 5,964,798 A | 10/1999 | Imran |
| 5,968,091 A | 10/1999 | Pinchuk |
| 5,968,093 A | 10/1999 | Kranz |
| 5,972,027 A | 10/1999 | Johnson |
| 5,980,553 A | 11/1999 | Gray |
| 6,010,530 A | 1/2000 | Goicoechea |
| 6,027,526 A * | 2/2000 | Limon et al. ............ 623/1.15 |
| 6,033,433 A | 3/2000 | Ehr et al. |
| 6,039,756 A | 3/2000 | Jang |
| 6,042,606 A | 3/2000 | Frantzen |
| 6,053,940 A | 4/2000 | Wijay |
| 6,066,169 A | 5/2000 | McGuinness |
| 6,106,548 A | 8/2000 | Roubin et al. |
| 6,113,627 A | 9/2000 | Jang |
| 6,117,165 A | 9/2000 | Becker |
| 6,123,721 A | 9/2000 | Jang |
| 6,129,755 A | 10/2000 | Mathis |
| 6,136,023 A | 10/2000 | Boyle |
| 6,152,957 A | 11/2000 | Jang |
| 6,156,052 A | 12/2000 | Richter |
| 6,162,243 A | 12/2000 | Gray |
| 6,179,868 B1 | 1/2001 | Burpee |
| 6,183,506 B1 | 2/2001 | Penn et al. |
| 6,190,403 B1 | 2/2001 | Fischell et al. |
| 6,190,404 B1 | 2/2001 | Palmaz et al. |
| 6,190,406 B1 | 2/2001 | Duerig |
| 6,193,744 B1 | 2/2001 | Ehr |
| 6,193,747 B1 | 2/2001 | vonOepen |
| 6,200,334 B1 | 3/2001 | Jang |
| 6,200,337 B1 | 3/2001 | Moriuchi |
| 6,203,569 B1 | 3/2001 | Wijay |
| 6,206,911 B1 | 3/2001 | Milo |
| 6,206,915 B1 | 3/2001 | Fagan et al. |
| 6,206,916 B1 | 3/2001 | Furst |
| 6,217,608 B1 | 4/2001 | Penn et al. |
| 6,221,319 B1 | 4/2001 | Johnson |
| 6,231,598 B1 | 5/2001 | Berry et al. |
| 6,235,053 B1 | 5/2001 | Jang |
| 6,241,760 B1 | 6/2001 | Jang |
| 6,251,134 B1 | 6/2001 | Alt |
| 6,254,632 B1 | 7/2001 | Wu et al. |
| 6,258,121 B1 | 7/2001 | Yang et al. |
| 6,261,319 B1 | 7/2001 | Kveen et al. |
| 6,261,320 B1 | 7/2001 | Tam et al. |
| 6,270,524 B1 | 8/2001 | Kim |
| 6,273,908 B1 | 8/2001 | Ndondo-Lay |
| 6,273,911 B1 | 8/2001 | Cox et al. |
| 6,273,913 B1 | 8/2001 | Wright et al. |
| 6,280,413 B1 | 8/2001 | Clark et al. |
| 6,309,413 B1 | 10/2001 | Dereume |
| 6,331,189 B1 | 12/2001 | Wolinsky |
| 6,348,065 B1 | 2/2002 | Brown et al. |
| 6,355,059 B1 | 3/2002 | Richter |
| 6,379,381 B1 | 4/2002 | Hossainy et al. |
| 6,409,761 B1 | 6/2002 | Jang |
| 6,416,538 B1 | 7/2002 | Ley |
| 6,423,090 B1 | 7/2002 | Hancock |
| 6,432,133 B1 | 8/2002 | Lau et al. |
| 6,443,982 B1 | 9/2002 | Israel |
| 6,451,049 B2 | 9/2002 | Vallana |
| 6,451,052 B1 | 9/2002 | Burmeister |
| 6,461,380 B1 | 10/2002 | Cox |
| 6,461,381 B2 | 10/2002 | Israel |
| 6,464,720 B2 | 10/2002 | Boatman |
| 6,464,722 B2 | 10/2002 | Israel |
| 6,468,302 B2 | 10/2002 | Cox |
| 6,471,720 B1 | 10/2002 | Ehr |
| 6,475,236 B1 | 11/2002 | Roubin |
| 6,478,816 B1 | 11/2002 | Kveen et al. |
| 6,485,508 B1 | 11/2002 | McGuinness |
| 6,689,159 B2 | 2/2004 | Lau |
| 6,764,506 B2 | 7/2004 | Roubin |
| 6,818,014 B2 * | 11/2004 | Brown et al. ............ 623/1.16 |
| 6,852,124 B2 | 2/2005 | Cox et al. |
| 6,964,679 B1 | 11/2005 | Marcade |
| 7,014,654 B2 | 3/2006 | Welsh |
| 7,326,241 B2 | 2/2008 | Jang |
| 2001/0010013 A1 | 7/2001 | Cox |
| 2001/0020183 A1 | 9/2001 | Jang |
| 2001/0035783 A1 | 11/2001 | Kanba |
| 2001/0056298 A1 | 12/2001 | Brown |
| 2002/0038145 A1 | 3/2002 | Jang |
| 2002/0042647 A1 | 4/2002 | Jang |
| 2002/0045933 A1 | 4/2002 | Jang |
| 2002/0045934 A1 | 4/2002 | Jang |
| 2002/0045935 A1 | 4/2002 | Jang |
| 2002/0049493 A1 | 4/2002 | Jang |
| 2002/0058990 A1 | 5/2002 | Jang |
| 2002/0161429 A1 | 10/2002 | Jang |
| 2002/0193870 A1 | 12/2002 | Jang |
| 2003/0028242 A1 | 2/2003 | Vallana |
| 2003/0083736 A1 | 5/2003 | Brown |
| 2003/0093144 A1 | 5/2003 | Jang |
| 2003/0208263 A1 | 11/2003 | Burmeister |
| 2004/0225347 A1 | 11/2004 | Lang |
| 2004/0267350 A1 | 12/2004 | Roubin |
| 2006/0195172 A1 | 8/2006 | Luo |

FOREIGN PATENT DOCUMENTS

| | | |
|---|---|---|
| DE | 29608037 U1 | 8/1996 |
| DE | 29701758 U1 | 5/1997 |
| DE | 29702671 U1 | 5/1997 |
| DE | 29708689 U1 | 8/1997 |
| DE | 29708879 U1 | 9/1997 |
| EP | 0183372 A1 | 6/1986 |

(56) References Cited

FOREIGN PATENT DOCUMENTS

| | | |
|---|---|---|
| EP | 0364787 A1 | 4/1990 |
| EP | 0364787 B1 | 4/1990 |
| EP | 0335341 B1 | 4/1992 |
| EP | 0540290 | 5/1993 |
| EP | 0540290 A2 | 5/1993 |
| EP | 0587197 A1 | 3/1994 |
| EP | 0606165 A1 | 7/1994 |
| EP | 0679372 A2 | 2/1995 |
| EP | 0709067 A2 | 1/1996 |
| EP | 0734698 A2 | 2/1996 |
| EP | 0821920 A1 | 2/1998 |
| EP | 0875215 A1 | 11/1998 |
| EP | 0950386 A2 | 10/1999 |
| EP | 0980694 A2 | 2/2000 |
| EP | 2079417 | 7/2009 |
| FR | 2785174 A1 | 5/2000 |
| JP | 6181993 | 7/1994 |
| WO | 9417754 | 8/1994 |
| WO | 9508975 A1 | 4/1995 |
| WO | 9531945 | 11/1995 |
| WO | 9532688 | 12/1995 |
| WO | 9603092 | 2/1996 |
| WO | 9603092 A1 | 2/1996 |
| WO | 9603029 | 8/1996 |
| WO | 9626689 | 9/1996 |
| WO | 9714375 | 4/1997 |
| WO | 9725937 | 7/1997 |
| WO | 9726840 | 7/1997 |
| WO | 9732543 | 9/1997 |
| WO | 9732544 | 9/1997 |
| WO | 9733534 | 9/1997 |
| WO | 9740780 | 11/1997 |
| WO | 9740781 | 11/1997 |
| WO | 9740782 | 11/1997 |
| WO | 9740783 | 11/1997 |
| WO | 9740784 | 11/1997 |
| WO | 9820810 A1 | 5/1998 |
| WO | 9823228 A1 | 6/1998 |
| WO | 9836784 A1 | 8/1998 |
| WO | 9840035 A1 | 9/1998 |
| WO | 9842278 | 10/1998 |
| WO | 9901088 A1 | 1/1999 |
| WO | 9915107 A1 | 4/1999 |
| WO | 9915108 A2 | 4/1999 |
| WO | 9923977 A1 | 5/1999 |
| WO | 9938457 A1 | 8/1999 |
| WO | 9940876 A2 | 8/1999 |
| WO | 9955253 A1 | 11/1999 |
| WO | 0003661 A1 | 1/2000 |
| WO | 0006051 | 2/2000 |
| WO | 0013611 A1 | 3/2000 |
| WO | 0028922 A1 | 5/2000 |
| WO | 0030563 A1 | 6/2000 |
| WO | 0062710 A1 | 10/2000 |
| WO | 0106954 A1 | 2/2001 |
| WO | 0126584 A1 | 4/2001 |
| WO | 0166036 A2 | 9/2001 |
| WO | 0191918 A1 | 12/2001 |
| WO | 0193781 A2 | 12/2001 |
| WO | 0224112 A2 | 3/2002 |

OTHER PUBLICATIONS

SECO online publication, "Get the Balance Rigt", Carboloy.com.
American Centrifugal Technical FAQs ACIPCO, American Cast Iron Pipe Company, (1995-2000).
Continued videotaped deposition of James E. Moore, Jr., Ph.D., held at the offices of Kirkland & Ellis, LLP, 153 East 53' Street, New York, New York, pursuant to adjournment, before Cary N. Bigelow, RPR, a Notary Public of the State of New York, dated Mar. 18, 2005,8:33 a.m. (Case No. 03-027-SLR).
Videotaped deposition of James E. Moore, Jr., Ph.D., held at the offices of Kirkland & Ellis, LLP, 153 East 53,d Street, New York, New York, pursuant to notice, before Cary N. Bigelow, RPR, a Notary Public of the State of New York, dated Mar. 17, 2005,9:32 a.m. (Case No. 03-027-SLR).
Corrected Rebuttal Expert Report of Professor James E. Moore Jr., Ph.D., dated Mar. 14, 2005 (Case No. 03-027-SLR).
Corrected Expert Report of Professor James E. Moore Jr., Ph.D., dated Feb. 2, 2005 (Case No. 03-027-SLR).
Opening Expert Report of Nigel Buller, B.SC, M.B., F.R.C.P. regarding Validity of the Jang Patent (Case No. 03-027-SLR).
Deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 2, 2005, 9:32 a.m. (Case No. 03-027-SLR).
Continued deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 3, 2005,8:45 a.m. (Case No. 03-027-SLR).
Rebuttal Expert Report of Nigel Buller, B.SC., M.B., F.R.C.P., dated Feb. 25, 2005 (Case No. 03-027-SLR).
Videotaped Deposition of the David Morre Parks, Ph.D., a witness called on behalf of the Defendants, pursuant to the Federal Rules of Civil Procedure, before Judith McGovern Williams, Certified Shorthand Reporter No. 130993, Registered Professional Reporter, Certified Realtime Reporter, and Notary Public in and for the Commonwealth of Massachusetts, at the Hyatt Regency, 575 Memorial Drive, Cambridge, Massachusetts, on Monday, Mar. 21, 2005.
Opening Expert Report of David M. Parks, Ph.D. Regarding Validity of the Jang Patent, dated Jan. 28, 2005 (Case No. 03-027-SLR).
Rebuttal Expert Report of David M. Parks, Ph.D., dated Feb. 25, 2005 (Case No. 03-027-SLR).
BSC's Opposition to Cordis' Motion for Summary Judgment of Non infringement of Claim 36 of the Jang '021 Patent, dated Apr. 14, 2005 (Case No. 03-027-SLR).
Redacted Version—Publicly Filed BSC's Opposition to Cordis' Motion for Summary Judgment of Non infringement of Claim 36 of the Jang '021 Patent, dated Apr. 14, 2005 (Case No. 03-027-SLR).
Redacted Public Version: Opening Brief in Support of Cordis' Motion for Summary Judgement of Noninfringement of Claim 36 of the Jang '021 Patent, dated Mar. 31, 2005 (Case No. 03-027-SLR).
Opening Brief in Support of Cordis' Motion for Summary Judgment of Non infringement of Claim 36 of the Jang '021 Patent, dated Mar. 24, 2005 (Case No. 03-027-SLR).
Reply Brief in Support of Cordis' Motion for Summary Judgment of Non infringement of the Jang '021 Patent, dated Apr. 21, 2005 (Case No. 03-027-SLR).
Order, dated Jun. 3, 2005 (Case No. 03" 027" SLR).
Jury Verdict, dated Jul. 1, 2005 (Case No. 03-027" SLR and Case No. 03-283-SLR).
Jury Trial—Volume H, BSC v. Cordis & J&J, CA #03" 27 & 03-283 (SLR), dated Friday, Jul. 1, 2005, pp. 1816-1857 and Index pp. 1-7.
Jury Trial—Volume A, BSC v. Cordis & J&J, CA #03-27 & 03" 283 (SLR), dated Tuesday, Jun. 21, 2005, pp. 1" 107 and Index pp. 1-12.
Jury Trial—Volume B, BSC v. Cordis & J&J, CA #03" 27 & 03" 283 (SLR), dated Wednesday, Jun. 22, 2005, pp. 108-407 and Index pp. 1" 32.
Jury Trial—Volume C, BSC v. Cordis & J&J, CA #03-27 & 03-283 (SLR), dated Thursday, Jun. 23, 2005, pp. 408-691 and Index pp. 1-29.
Jury Trial—Volume D, BSC v. Cordis & J&J, CA #03" 27 & 03" 283 (SLR), dated Friday, Jun. 24, 2005, pp. 693-930 and Index pp. 1-23.
Jury Trial—Volume E, BSC v. Cordis & J&J, CA #03" 27 & 03-283 (SLR), dated Jun. 28, 2005, pp. 931-1223.
Under Seal—Volume EE, BSC v. Cordis & J&J, CA #03-27 & 03" 283 (SLR), dated Tuesday Jun. 28, 2005, pp. 1-61 and Index pp. 1-8.
Jury Trial—Volume F, BSC v. Cordis & J&J, CA #03" 27 & 03" 283 (SLR), dated Wednesday, Jun. 29, 2005, pp. 1224-1537 and Index pp. 1-32.
Jury Trial—Volume G, BSC v. Cordis & J&J, CA #03" 27 & 03" 283 (SLR), dated Thursday, Jun. 30, 2005, pp. 1538" 1815 and Index pp. 1-30.

(56) References Cited

OTHER PUBLICATIONS

Manufacturing Processes for Engineering Materials, by Serope Kalpakjian, Illinois Institute of Technology, Addison—Wesley Publishing Company, pp. 340, Date Unknown.

A View of Vascular Stents, by Richard A. Schatz, MD, From the Arizona Heart Institute Foundation, Phoenix, Arizona, Circulation: vol. 79, No. 2, Feb. 1989, pp. 445-457.

The Self-Expanding Mesh Stent, by Ulrich Sigwart, Section IV Chapter 29, pp. 605-610.

Improved Dilation Catheter Balloons, by Stanley B. Levy PhD., Journal of Clinical Engineering, vol. 11, No. 4, Jul.-Aug. 1986, pp. 291-296.

Technical Note Entitled Modifications of Gianturco Expandable Wire Stents, by Barry T. Uchida et al., AJR, vol. 150, May 1988, pp. 1185-1187.

Brochure from Cook Incorporated regarding Gianturco-Rosch Biliary Z-Stents TM, 1989.

Expandable Biliary Endoprosthesis: An Experimental Study, by Carrasco et al., AJR vol. 145, Dec. 1985, pp. 1279-1282.

Tracheobronchial Tree: Expandable Metallic Stents Used in Experimental and Clinical Applications\, Work in Progress, by Wallace et al, Radiology, Feb. 1986, pp. 309-312.

Brochure Entitled Ave Micro Stent TM, Instructions for Use, by Applied Vascular Engineering, Inc., pp. 1-15.

Brochure Entitled Micro StentTM, by Applied Vascular Engineering, Inc., Date Unknown.

Japanese Infringements Search on Articulated Expandable Stents, dated Jul. 12, 1995.

Engineering Fluid Mechanics, Third Edition, John A. Roberson and Clayton T Crowe, pp. 94 and pp. 414-421, Date Unknown.

Cambridge Dictionary of Science and Technology, Cambridge University Pres. 128, Date Unknown.

Beyar et al, "The BeStent; The Parallel-Serial Jang Stents", Handbook of Coronary Stents, Second Edition, 158-171 & 229-234 (1998).

Beyar et al "Newer Stents; Material and Designs" IAGS Proceedings 9(5): 363-371 (Jun. 1997).

Roguin et al Acute and 30-Day Results of the Serpentine Balloon Expandable Stent Implantation in Simple and Complex Coronary Arterial Narrowing\, The American Journal of Cardiology, 80: 1155-1162 (Nov. 1997).

Roguin et al, "BeStent—the serpentine balloon expandable stent; review of mechanical properties and clinical experience", Astif Organs, 22(3):243-249 (Mar. 1998).

Brochure Entitled Sorin Biomedica "Carbostent TM".

* cited by examiner

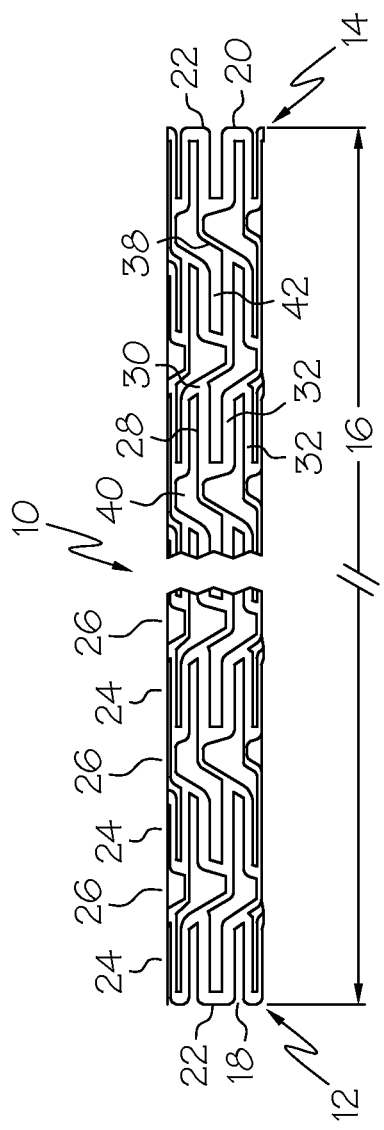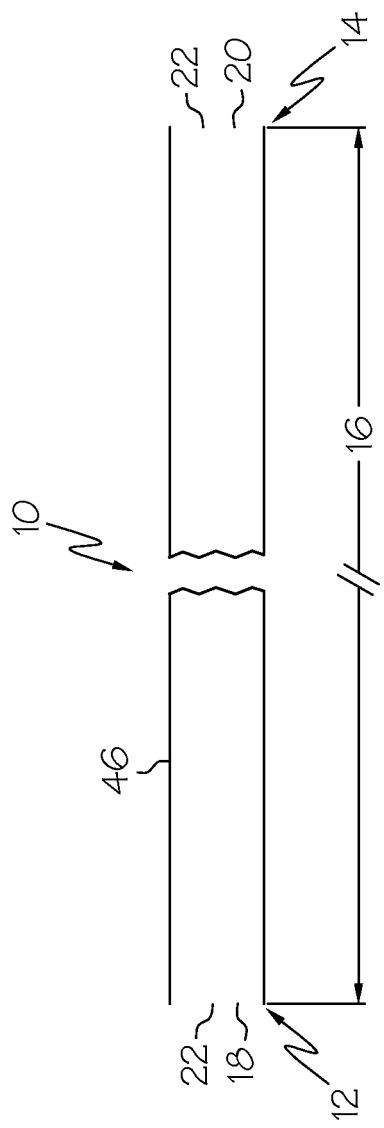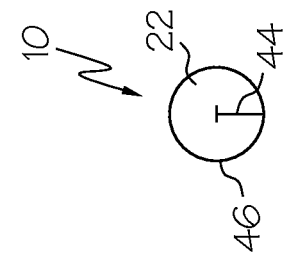

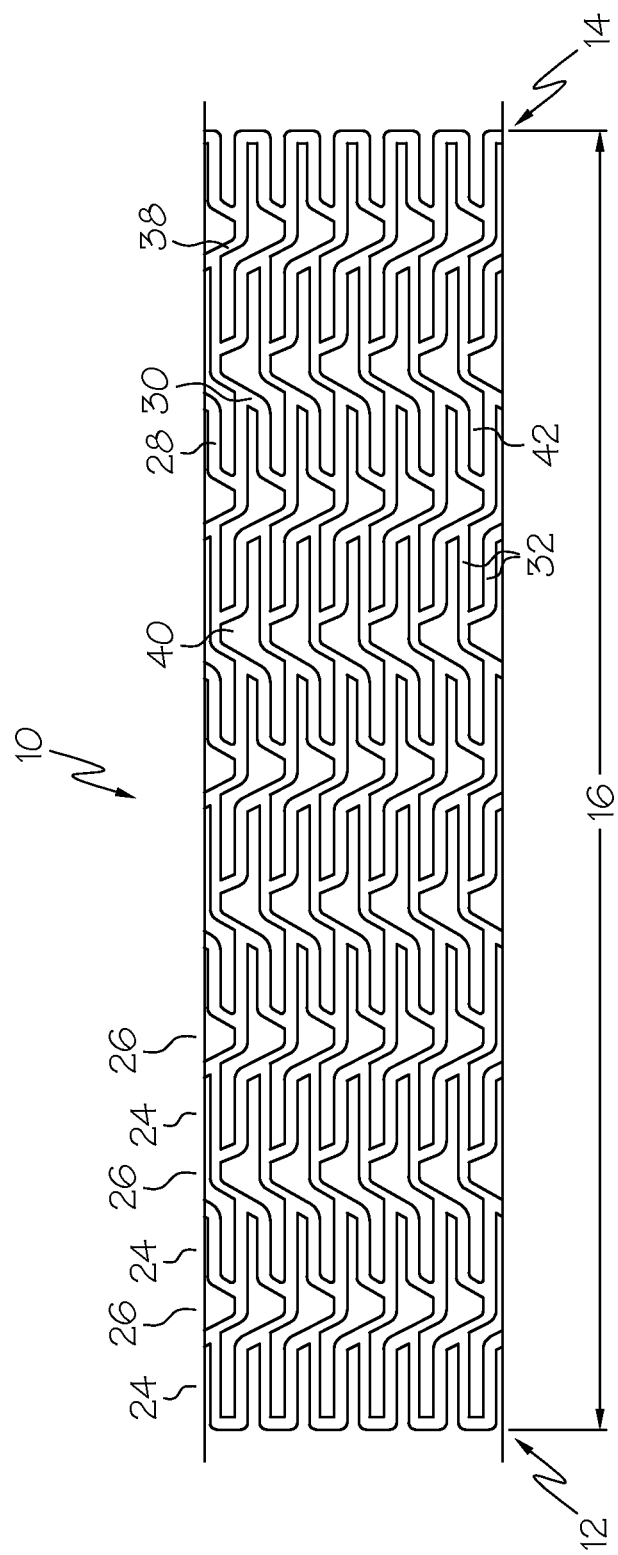

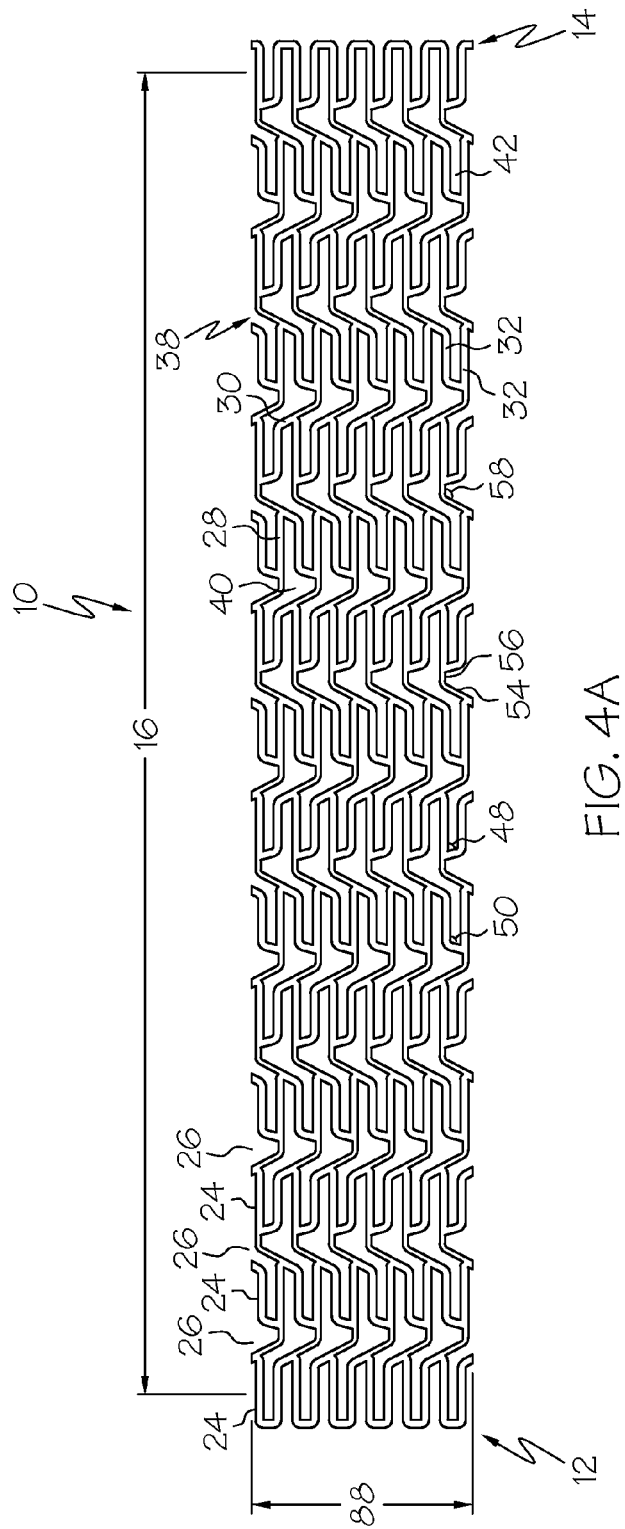
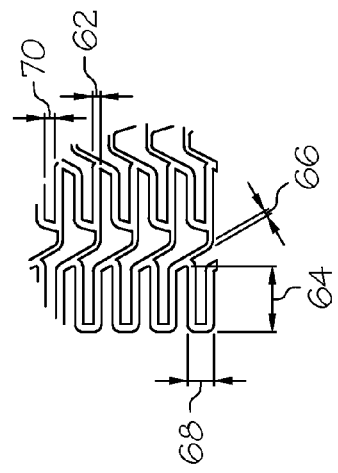
FIG. 4A
FIG. 4B

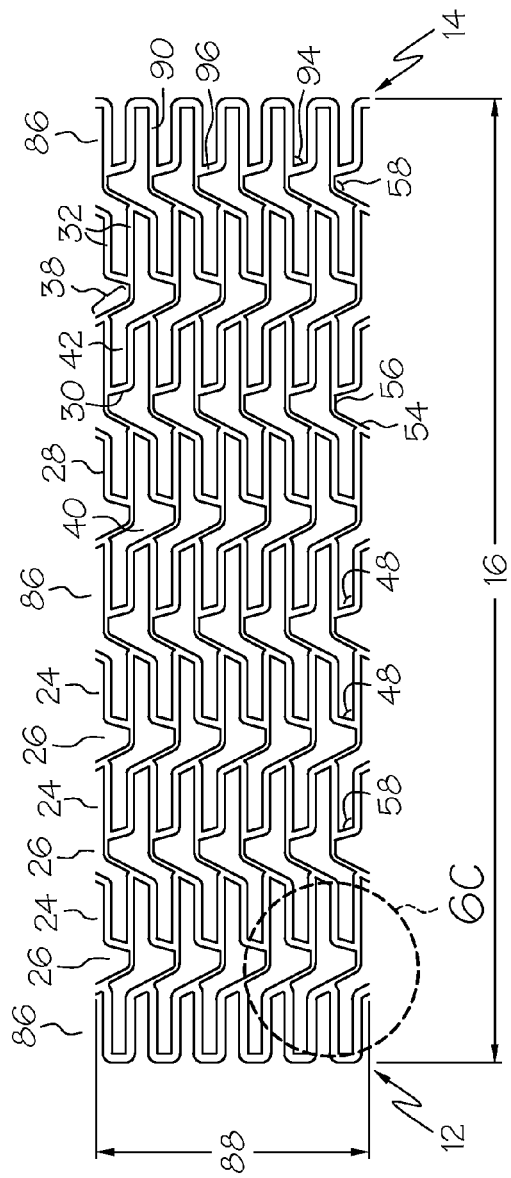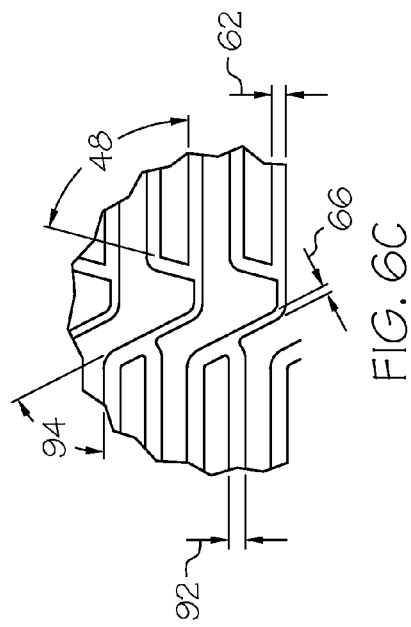

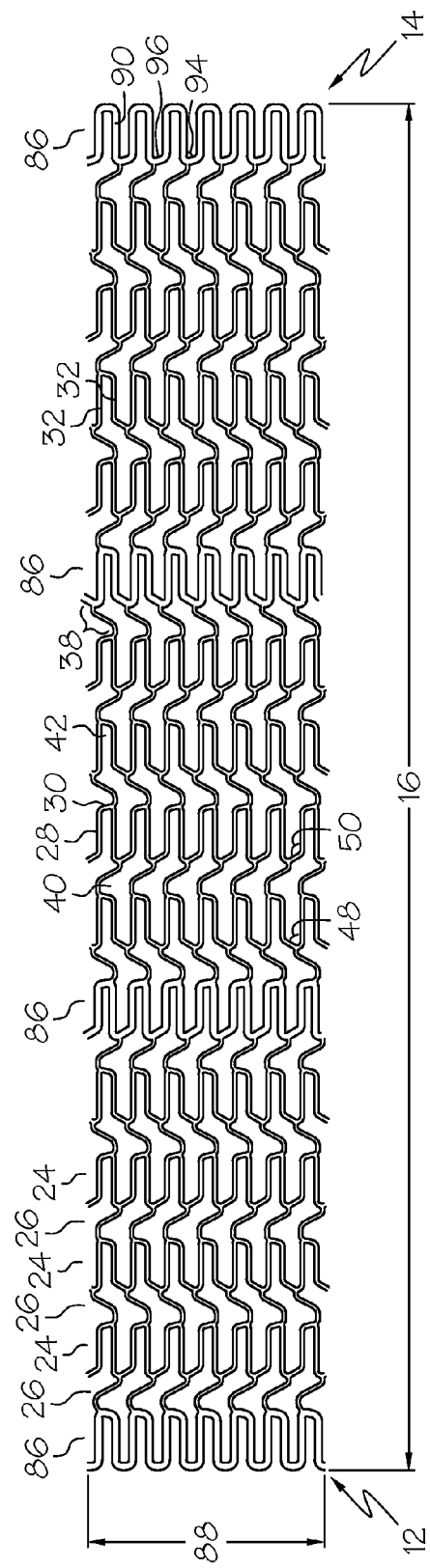

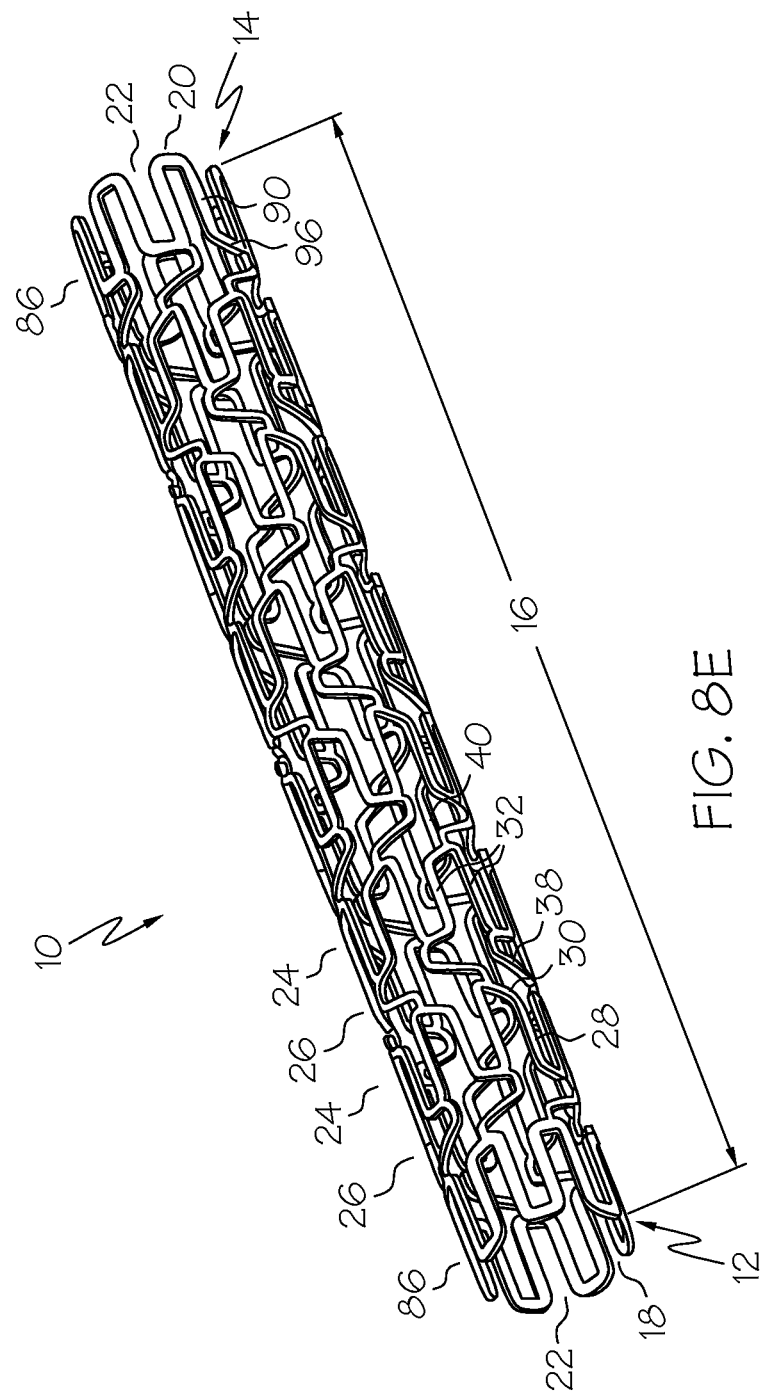

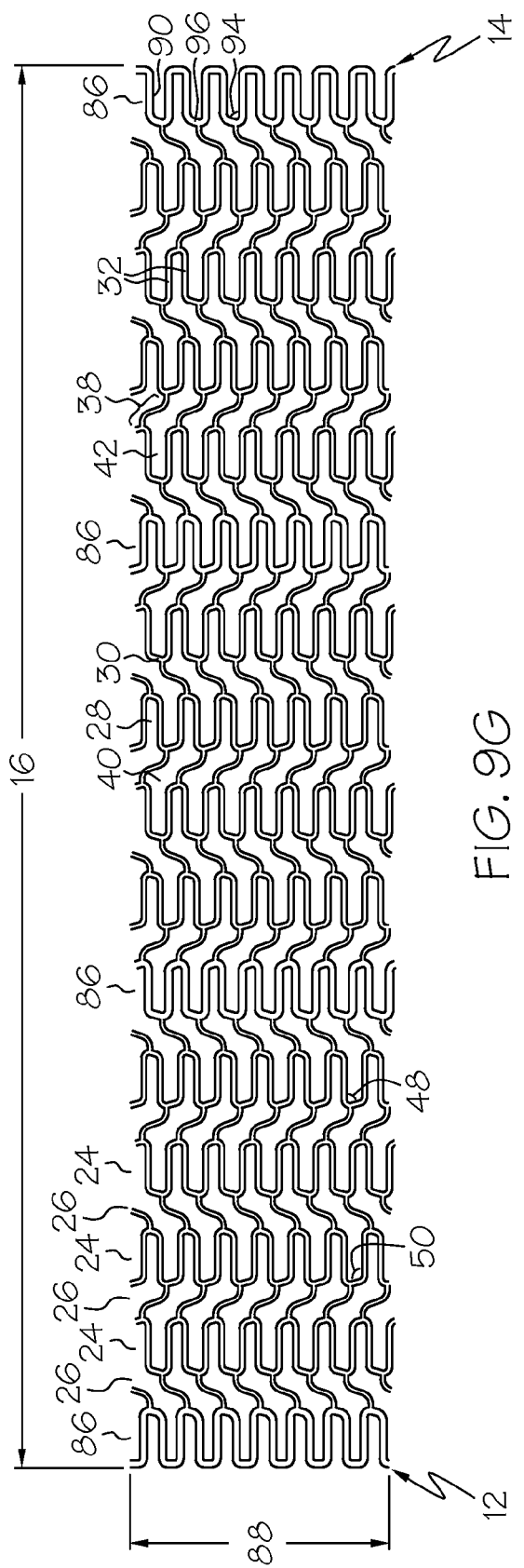

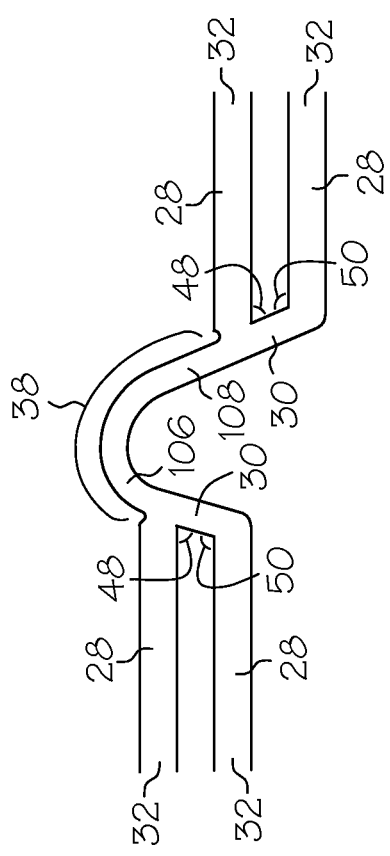
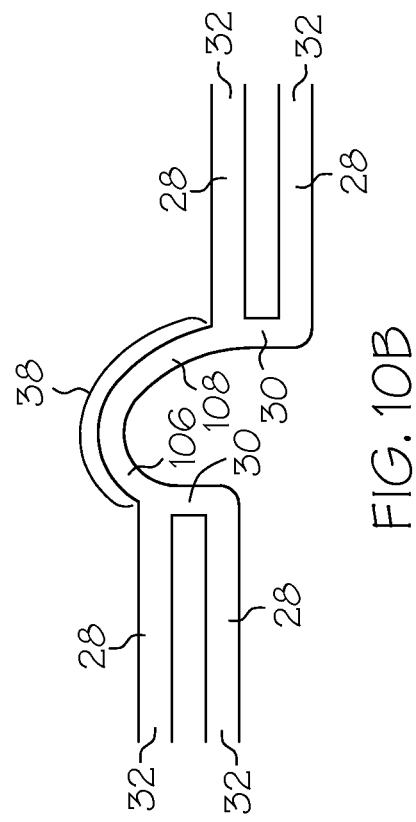
FIG. 10A
FIG. 10B

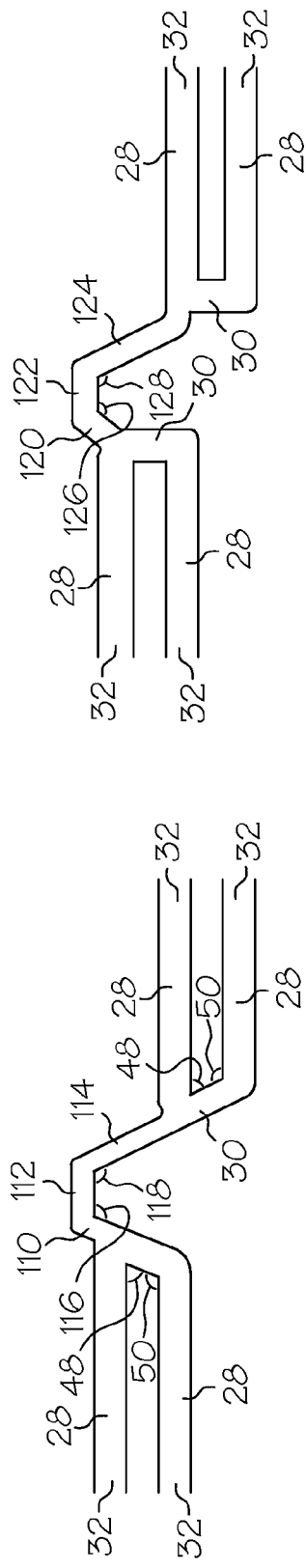
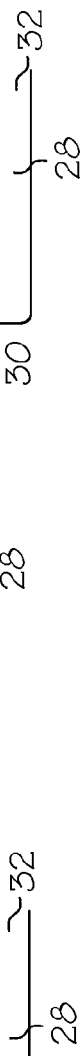
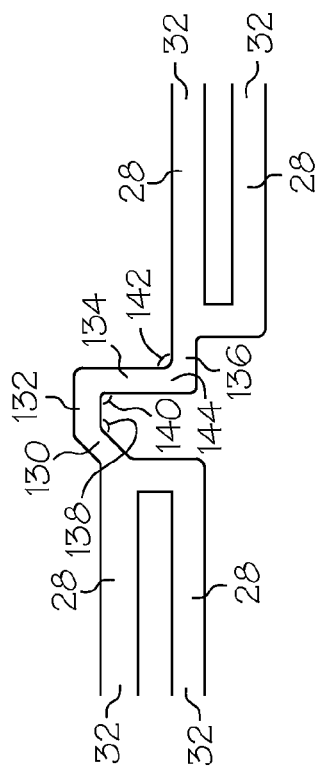
FIG. 10C
FIG. 10D
FIG. 10E

INTRAVASCULAR STENT

CROSS-REFERENCE TO RELATED APPLICATIONS

This application is a Continuation of U.S. patent application Ser. No. 10/206,432, filed on Jul. 25, 2002, which is a Continuation of U.S. patent application Ser. No. 09/574,077, filed on May 18, 2000, now U.S. Pat. No. 6,770,088, which is a Continuation-in-part of U.S. patent application Ser. No. 08/845,657, filed on Apr. 25, 1997, now U.S. Pat. No. 5,922,021, which is a Continuation of U.S. patent application Ser. No. 08/845,734, filed on Apr. 25, 1997, which is a Continuation-in-part of U.S. patent application Ser. No. 08/824,865, filed on Mar. 26, 1997, now U.S. Pat. No. 6,152,957, which is a Continuation-in-part of Ser. No. 08/824,866, filed on Mar. 26, 1997, now U.S. Pat. No. 5,954,743, which is a Continuation-in-part of U.S. patent application Ser. No. 08/824,142, filed on Mar. 25, 1997, now U.S. Pat. No. 6,241,760, which claims Priority from Provisional Application No. 60/017,484, filed on Apr. 26, 1996, all of which are incorporated herein by reference.

BACKGROUND OF THE INVENTION

1. Field of the Invention

This invention relates to intravascular stents, and more particularly to an intravascular stent which provides easy introduction through tortuous sections of vessels.

2. Description of the Related Art

Angioplasty, either coronary or general vascular, has advanced to become the most effective means for revascularization of stenosed vessels. In the early 1980's, angioplasty first became available for clinical practice in the coronary artery, and has since proven an effective alterative to conventional bypass graft surgery. Balloon catheter dependent angioplasty has consistently proven to be the most reliable and practical interventional procedure. Other ancillary technologies such as laser based treatment, or directional or rotational arthrectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational arthrectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for unstented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the multilink design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent, and no method of reenforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube. Adjacent first meander patterns are connected by second meander patterns to form a generally uniform distributed pattern. The symmetrical arrangement with first and second meander patterns having sharp right angled bends allows for catching and snagging on the vessel wall during delivery. Furthermore, the large convolutions in the second meander pattern are not fully straightened out during expansion reducing rigidity and structural strength of the expanded stent. There is, further, no method of programming the stent diameter along its longitudinal axis to achieve a tapering stent design, and no method of reenforcement of stent ends or other regions is provided for.

These and other conventional stent designs suffer in varying degrees from a variety of drawbacks including: (a) inability to negotiate bends in vessels due to columnar rigidity of the unexpanded stent; (b) lack of structural strength, axio-lateral, of the unexpanded stent; (c) significant foreshortening of the stent during expansion; (d) limited stent length; (e) constant expanded stent diameter; (f) poor crimping characteristics; and (g) rough surface modulation of the unexpanded stent.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent which, (i) can be crimped tightly on the expansion balloon while maintaining a low profile and flexibility, (ii) has a smooth surface modulation when crimped over a delivery balloon, to prevent catching and snagging of the stent on the vessel wall during delivery or (iii) with reenforcement rings on the ends or middle or both to keep the ends of the stent securely positioned against the vessel walls of the target blood vessel.

SUMMARY OF THE INVENTION

Accordingly an object of the present invention is to provide a scaffold for an interior lumen of a vessel.

Another object of the invention is to provide a stent which prevents recoil of the vessel following angioplasty.

A further object of the invention is to provide a stent that maintains a larger vessel lumen compared to the results obtained only with balloon angioplasty.

Yet another object of the invention is to provide a stent that reduces foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduced tuliping of a stent frame.

Another object of the invention is to provide a chain mesh stent that reduces vessel "hang up" in a tortuous vessel or a vessel with curvature.

A further object of the invention is to provide a chain mesh stent that increases radial and axio-lateral strength of the expanded stent.

These and other objects of the invention are achieved in a stent in a nonexpanded state. A first expansion column includes of a plurality of first expansion column strut pairs. A first expansion strut pair includes a first expansion strut adjacent to a second expansion strut and a first joining strut that couples the first and second expansion struts at a proximal end of the first expansion strut pair. A second expansion strut pair includes a third expansion strut adjacent to the second expansion strut and a second joining strut that couples the second and third expansion struts at a distal end of the second expansion strut pair. A third expansion strut pair includes a fourth expansion strut adjacent to the third expansion strut and a third joining strut that couples the third and fourth expansion struts at a proximal end of the third expansion strut pair. A fourth expansion strut pair includes a fifth expansion strut adjacent to the fourth expansion strut and a fourth joining strut that couples the fourth and fifth expansion struts at a distal end of the fourth expansion strut pair.

A first expansion strut pair first corner is formed where the first joining strut is coupled to the first expansion strut, and a first expansion strut pair second corner is formed where the first joining strut is coupled to the second expansion strut. A second expansion strut pair first corner is formed where the second joining strut is coupled to the second expansion strut, and a second expansion strut pair second corner is formed where the second joining strut is coupled to the third expansion strut. A third expansion strut pair first corner is formed where the third joining strut is coupled to the third expansion strut, and a third expansion strut pair second corner is formed where the third joining strut is coupled to the fourth expansion strut. A fourth expansion strut pair first corner is formed where the fourth joining strut is coupled to the fourth expansion strut, and a fourth expansion strut pair second corner is formed where the fourth joining strut is coupled to the fifth expansion strut.

A second expansion column includes of a plurality of second expansion column strut pairs. A first expansion strut pair includes a first expansion strut adjacent to a second expansion strut and a first joining strut that couples the first and second expansion struts at a proximal end of the first expansion strut pair. A second expansion strut pair includes a third expansion strut adjacent to the second expansion strut and a second joining strut that couples the second and third expansion struts at a distal end of the second expansion strut pair. A third expansion strut pair includes a fourth expansion strut adjacent to the third expansion strut and a third joining strut that couples the third and fourth expansion struts at a proximal end of the third expansion strut pair. A fourth expansion strut pair includes a fifth expansion strut adjacent to the fourth expansion strut and a fourth joining strut that couples the fourth and fifth expansion struts at a distal end of the fourth expansion strut pair.

A first expansion strut pair first corner is formed where the first joining strut is coupled to the first expansion strut, and a first expansion strut pair second corner is formed where the first joining strut is coupled to the second expansion strut. A second expansion strut pair first corner is formed where the second joining strut is coupled to the second expansion strut, and a second expansion strut pair second corner is formed where the second joining strut is coupled to the third expansion strut. A third expansion strut pair first corner is formed where the third joining strut is coupled to the third expansion strut, and a third expansion strut pair second corner is formed where the third joining strut is coupled to the fourth expansion strut. A fourth expansion strut pair first corner is formed where the fourth joining strut is coupled to the fourth expansion strut, and a fourth expansion strut pair second corner is formed where the fourth joining strut is coupled to the fifth expansion strut.

A first connecting strut column is formed of a plurality of first connecting struts, each connecting strut of the first connecting strut column includes a connecting strut proximal section, a connecting strut distal section and a connecting strut intermediate section. A first connecting strut proximal section is coupled to the first corner of the second expansion strut pair of the first expansion strut column, and a first connecting strut distal section is coupled to the first joining strut of the first expansion strut pair of the second expansion strut column intermediate the first expansion strut pair first corner and the first expansion strut pair second corner. A second connecting strut proximal section is coupled to the first corner of the fourth expansion strut pair of the first expansion strut column, and a second connecting strut distal section is coupled to the third joining strut of the third expansion strut pair of the second expansion strut column intermediate the third expansion strut pair first corner and the third expansion strut pair second corner.

BRIEF DESCRIPTION OF THE DRAWINGS

FIG. 1A is a side elevation view of the pre-expansion mode of an embodiment of the stent of the present invention;

FIG. 1B is a cross sectional view of an embodiment of the stent of the present invention;

FIG. 1C is a longitudinal cross sectional view of an embodiment of the stent of the present invention;

FIG. 2A is a scale drawing of the strut pattern of an embodiment of the stent of the present invention;

FIG. 4A is a scale drawing including dimensions of an embodiment of the stent of the present invention;

FIG. 4B is an enlarged section of the scale drawing of FIG. 4A;

FIG. 6A is a scale drawing of an embodiment of the stent of the present invention with reenforcement expansion columns;

FIG. 6C is an expanded view of a section of the pattern of FIG. 6A;

FIG. 8C is a scale drawing of an embodiment of the stent of the present invention;

FIG. 8E is a perspective view of the embodiment of FIG. 8D;

FIG. 9G is an enlarged view of a single connecting strut joining two expansion strut pairs in accordance with an embodiment of the present invention;

FIG. 10A is a drawing of an alternate geometry of connecting struts and joining struts in accord with the present invention;

FIG. 10B is a drawing of an alternate geometry of connecting struts and joining struts in accord with the present invention;

FIG. 10C is a drawing of an alternate geometry of connecting struts and joining struts in accord with the present invention;

FIG. 10D is a drawing of an alternate geometry of connecting struts and joining struts in accord with the present invention;

FIG. 10E is a drawing of an alternate geometry of connecting struts and joining struts in accord with the present invention;

DETAILED DESCRIPTION

Figure 2B:
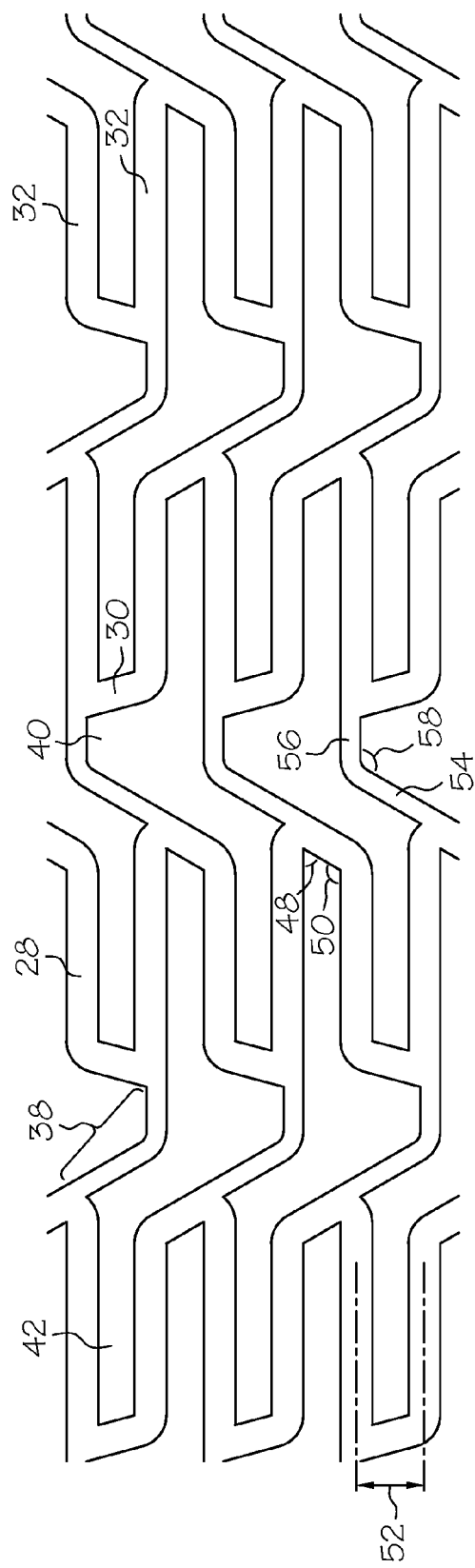
FIG. 2B is an expanded view of a section of the pattern of FIG. 2A.

A first embodiment of the present invention is shown in FIGS. 1A, 1B, 1C, 2A and 2B. Referring to FIG. 1A, an elongate hollow tubular stent 10 in an unexpanded state is shown. A proximal end 12 and a distal end 14 define a longitudinal length 16 of stent 10. The longitudinal length 16 of the stent 10 can be as long as 100 mm or longer. A proximal opening 18 and a distal opening 20 connect to an inner lumen 22 of stent 10. Stent 10 can be a single piece, without any seams or welding joints or may include multiple pieces.

Stent 10 is constructed of two to fifty or more expansion columns or rings 24 connected together by interspersed connecting strut columns 26. The first column on the proximal end 12 and the last column on the distal end 14 of stent 10 are expansion columns 24.

Expansion columns 24 are formed from a series of expansion struts 28, and joining struts 30. Expansion struts 28 are thin elongate members arranged so that they extend at least in part in the direction of the longitudinal axis of stent 10. When an outward external force is applied to stent 10 from the inside by an expansion balloon or other means, expansion struts 28 are reoriented such that they extend in a more circumferential direction, i.e along the surface of cylindrical stent 10 and perpendicular to its longitudinal axis. Reorientation of expansion struts 28 causes stent 10 to have an expanded circumference and diameter. In FIG. 1A, expansion struts 28 of unexpanded stent 10 are seen to extend substantially parallel to the longitudinal axis of stent 10.

Expansion struts 28 are joined together by joining struts 30 to form a plurality of expansion strut pairs 32. Expansion strut pairs have a closed end 34 and an open end 36. Additional joining struts 30 join together expansion struts 28 of adjacent expansion strut pairs 32, such that expansion struts 28 are joined alternately at their proximal and distal ends to adjacent expansion struts 28 to form expansion columns 24. Each expansion column 24 contains a plurality, typically eight to twenty, twenty to sixty, or larger of expansion struts 28. Expansion columns are preferably continuous unbroken ring structures extending around the circumference of the stent 10; however, broken structures in which individual struts or pieces of struts are removed from an otherwise continuous expansion column 24 can also be used.

Connecting struts 38 connect adjacent expansion columns 24 forming a series of interspersed connecting strut columns 26 each extending around the circumference of stent 10. Each connecting strut 38 joins a pair of expansion struts 28 in an expansion column 24 to an adjacent pair of expansion struts 28 in an adjacent expansion column 24. For stent 10 of FIG. 1A, the ratio of expansion struts 28 in an expansion column 24 to connecting struts 38 in a connecting strut column 26 is two to one; however, this ratio in general can be x to 1 where x is greater or less than two. Furthermore, since the stent 10 of FIG. 1A begins with an expansion column 24 on the proximal end 12 and ends with an expansion column 24 on the distal end 14, if there are n expansion columns 24 with m expansion struts 28 per column, there will be m-1 connecting strut columns 26, and n(m-1)/2 connecting struts 38.

The reduced number of connecting struts 38 in each connecting strut column 26, as compared to expansion struts 28 in each expansion column 24, allows stent 10 to be longitudinally flexibility. Longitudinal flexibility can be further increased by using a narrow width connecting strut, providing additional flexibility and suppleness to the stent as it is navigated around turns in a natural blood vessel.

At least a portion of the open spaces between struts in stent 10 form asymmetrical cell spaces 40. A cell space or geometric cell is an empty region on the surface of stent 10, completely surrounded by one or a combination of stent struts, including expansion struts 28, connecting struts 38, or joining struts 30. Asymmetrical cell spaces 40 are cell spaces which have no geometrical symmetry i.e. no rotation, reflection, combination rotation and reflection or other symmetry. Asymmetrical cell spaces 40 have an asymmetrical geometric configuration.

Asymmetrical cell spaces 40 in FIG. 1A are surrounded by a first expansion strut pair 32 in a first expansion column 24, a first connecting strut 38, a second expansion strut pair 32 in an adjacent expansion column 24, a first joining strut 30, a second connecting strut 38, and a second joining strut 30. Furthermore, expansion strut pairs 32 of asymmetrical cell space 40 may be circumferentially offset i.e. have longitudinal axes that are not collinear and have their open ends 36 facing each other. The space between two expansion struts of an expansion strut pair 32 is known as a loop slot 42.

FIG. 1B shows inner lumen 22, radius 44 and stent wall 46 of stent 10. Stent wall 46 consists of stent struts including expansion struts 28, connecting struts 38 and joining struts 30.

FIG. 1C shows, proximal end 12, distal end 14, longitudinal length 16, inner lumen 22, and stent wall 46 of stent 10. Inner lumen 22 is surrounded by stent wall 46 which forms the cylindrical surface of stent 10.

Referring now to FIGS. 2A and 2B, joining struts 30 of stent 10 are seen to extend at an angle to the expansion struts 28, forming a narrow angle 48 with one expansion strut 28 in an expansion strut pair 32 and a wide angle 50 with the other expansion strut 28 of an expansion strut pair 32. Narrow angle 48 is less than ninety degrees, while wide angle 50 is greater than ninety degrees. Joining struts 30 extend both longitudinally along the longitudinal axis of stent 10 and circumferentially, along the surface of the stent 10 perpendicular to its longitudinal axis.

Expansion strut spacing 52 between adjacent expansion struts 28 in a given expansion column 24 are uniform in stent 10 of FIGS. 2A and 2B; however, non-uniform spacings can also be used. Expansion strut spacings 52 can be varied, for example, spacings 52 between adjacent expansion struts 28 in an expansion column 24 can alternate between a narrow and a wide spacings. Additionally, spacings 52 in a single expansion column 24 can differ from other spacings 52 in other columns 24.

It is noted that varying expansion strut spacings 52 which form the loop slots 42 results in variable loop slot widths. Furthermore, the longitudinal axis of the loop slots 42 need not be collinear or even parallel with the longitudinal axis of loop slots 42 of an adjacent expansion column 24. FIGS. 2A and 2B show an arrangement of expansion struts 28 such that collinear, parallel adjacent loop slots 42 are formed, but non-collinear and non-parallel loop slots 42 can also be used.

Additionally the shape of loop slots 42 need not be the same among loop slots of a single or multiple expansion columns 24. The shape of loop slots 42 can be altered by changing the orientation or physical dimensions of the expansion struts 28 and/or joining struts 30 which connect expansion struts 28 of expansion strut pairs 32 defining the boundaries of loop slots 42.

Connecting struts 38 couple adjacent expansion columns 24, by connecting the distal end of an expansion strut pair in one expansion column 24 to the proximal end of an adjacent expansion strut pair 32 in a second expansion column 24. Connecting struts 38 of FIGS. 2A and 2B are formed from two linear sections, a first linear section 54 being joined at its distal end to a second linear section 56 at its proximal end to form a first slant angle 58.

The first linear section 54 of a connecting strut 38 is joined to expansion strut 28 at the point where joining strut 30 makes narrow angle 48 with expansion strut 28. First linear section 54 extends substantially collinear to joining strut 30 continuing the line of joining strut 30 into the space between expansion columns 24. The distal end of the first linear section 54 is joined to the proximal end of the second linear section 56 forming slant angle 58. Second linear section 56 extends substantially parallel to expansion struts 28 connecting at its distal end to joining strut 30 in an adjacent expansion column 24. The distal end of second linear section 56 attaches to expansion strut 28 at the point where joining strut 30 makes narrow angle 48 with expansion strut 28. Further, joining strut 30 can have a second slant angle with a width that can be the same or different from the width of the first slant angle.

FIGS. 2A and 2B show connecting struts 38 and joining struts 30 slanted relative to the longitudinal axis of stent 10, with the circumferential direction of the slanted struts alternating from column to adjacent column. Circumferential direction refers to the handedness with which the slanted struts wind about the surface of the stent 10. The circumferential direction of the slant of connecting strut first linear sections 54 in a connecting strut column 26 is opposite the circumferential direction of the slant of connecting strut first linear sections 54 in an adjacent connecting strut column 26. Similarly, the circumferential direction of the slant of joining struts 30 in an expansion column 24 is opposite the circumferential direction of the slant of joining struts 30 in an adjacent expansion column 24. Alternating circumferential slant directions of connecting struts 38 and joining struts 30 prevents axial warping of stent 10 during deliver and expansion. Other non-alternating slant direction patterns can also be used for connecting struts 38 or joining struts 30 or both.

Figure 3B:
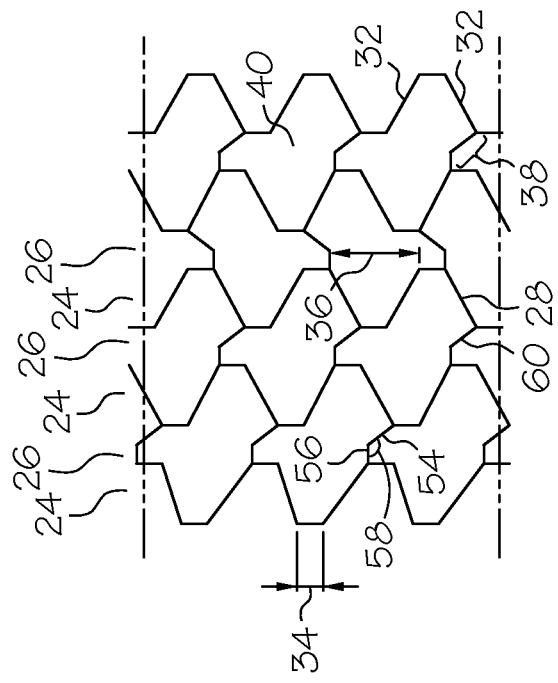
FIG. 3B is a schematic illustration of the post-expansion mode of an embodiment of the stent of the present invention.
Figure 3A:
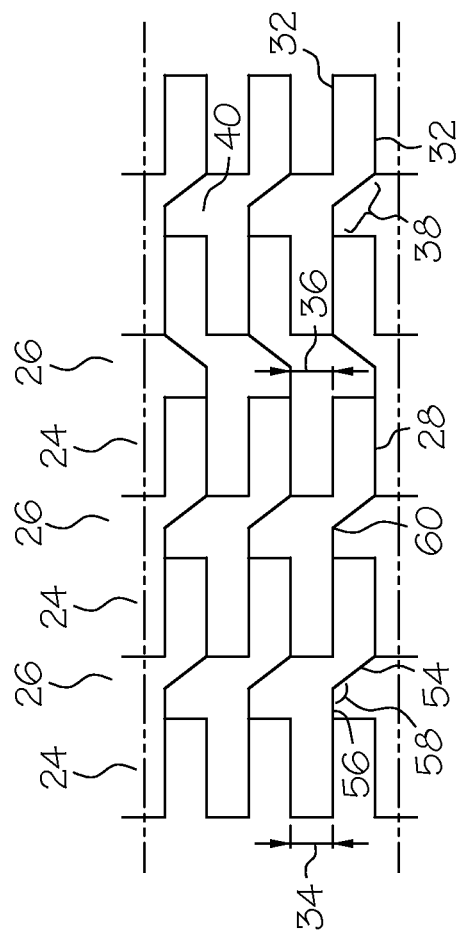
FIG. 3A is a schematic illustration of a pre-expansion mode of an embodiment of the stent of the present invention.

FIGS. 3A and 3B show a schematic illustration of a stent design according to the present invention in an unexpanded and expanded state respectively. The design is depicted as a flat projection, as if stent 10 were cut lengthwise parallel to its longitudinal axis and flattened out. The connecting struts 38 consist of first and second linear sections 54 and 56 forming slant angle 58 at pivot point 60. An asymmetrical cell space 40 is formed by expansion strut pairs 32, connecting struts 38 and joining struts 30. Multiple interlocking asymmetrical cell spaces 40 make up the design pattern.

As the stent is expanded, see FIG. 3B, the expansion strut pairs 32 spread apart at their open ends 36, shortening the length of expansion struts 28 along the longitudinal axis of the cylindrical stent. The longitudinal shortening of expansion struts 28 during expansion is countered by the longitudinal lengthening of connecting struts 38. The widening of slant angle 58 during expansion straightens connecting struts 38 and lengthens the distance between the coupled expansion strut pairs 32. The widening of the slant angle of connecting struts 38 substantially compensates for the longitudinal shortening of expansion struts 28. Thus, the stent has substantially constant unexpanded and expanded longitudinal lengths.

When the stent is expanded, each expansion column 24 becomes circumferentially stretched, enlarging the space between struts. The interlinking of expansion columns 24 by connecting struts 38 that have been straightened through the expansion process gives the stent 10 a high radial support strength. The entire stent 10 when expanded is unitized into a continuous chain mesh of stretched expansion columns 24 and connecting strut columns 26 forming an asymmetrical interlocking cell geometry which resists collapse both axially and radially. When the stent is expanded it has increased rigidity and fatigue tolerance.

In addition, efficient bending and straightening of connecting struts 38 at pivot points 60 allows increased longitudinal flexibility of the stent. For the stent to bend longitudinally, at least some of connecting struts 38 are forced to bend in their tangent plane. The tangent plane of a specific connecting strut 38 refers to the plane substantially tangent to the cylindrical surface of the stent at that connecting strut 38. The width of connecting struts 38 can be twice as wide as a thickness. Preferably, a one-to-one ratio is preferred. However, pivot points 60 in connecting struts 38 provide connecting struts 38 a flexible joint about which to more easily bend increasing longitudinal flexibility of the stent.

Referring to FIGS. 4A and 4B, a variation of the first embodiment of stent 10 of the present invention is shown. In this variation, stent 10 has a length 16 of 33.25 mm and an uncrimped and unexpanded circumference 88 of 5.26 mm. Fifteen expansion columns 24 are interspersed with connecting strut columns 26. Each expansion column 24 consists of twelve expansion struts 28 joined alternately at their proximal and distal ends by joining struts 30 forming six expansion strut pairs 32. Expansion struts 28 are aligned parallel to the longitudinal axis of cylindrical stent 10. Joining struts 30 form a narrow angle 48 and a wide angle 50 with the respective expansion struts 28 of expansion strut pairs 32. Adjacent expansion columns 24 employ alternating circumferential slant directions of joining struts 30.

In this variation of the first embodiment, expansion strut width 62 is 0.20 mm, expansion strut length 64 is 1.51 mm, and connecting strut width 66 is 0.13 mm. Distance 68 from the outer edge of a first expansion strut 28 to the outer edge of a second adjacent expansion strut 28 in the same expansion column 24 is 0.64 mm, leaving a loop slot width 70 of 0.24 mm.

In this variation of the first embodiment, connecting struts 38 consist of a slanted first linear section 54 joined to a second linear section 56 at a slant angle 58. First linear section 54 is slightly longer than second linear section 56 and is attached at its proximal end to an expansion strut 28 in an expansion column 24. The attachment of the proximal end of first linear section 54 to expansion strut 28 is at the point where joining strut 30 makes narrow angle 48 with expansion strut 28. First linear section 54 extends substantially collinear to joining strut 30 attaching at its distal end to the proximal end of second linear section 56 to form slant angle 58. Second linear section 56 extends substantially collinear to expansion struts 28, attaching at its distal end to an expansion strut 28 in an adjacent expansion column 24. The attachment occurs at the point where expansion strut 28 forms narrow angle 48 with joining strut 30. Joining struts 30 and connecting strut first linear sections 54 slant in alternating circumferential directions from column to adjacent column.

The joining of connecting struts 38 and expansion struts 28 at the point where narrow angle 48 is formed aids smooth delivery of stent 10 by streamlining the surface of the unexpanded stent and minimizing possible catching points. Bare delivery of stent 10 to the target lesion in a vessel will thus result in minimal snagging or catching as it is navigated through turns and curvatures in the vessel. Stent 10 behaves like a flexible, tubular sled as it is moved forward or backward in the vessel on the delivery catheter, sliding through tortuous vessels and over irregular bumps caused by atherosclerotic plaques inside the vessel lumen.

When fully expanded Stent 10 of FIGS. 4A and 4B has an internal diameter of up to 5.0 mm, while maintaining an acceptable radial strength and fatigue tolerance. The crimped stent outer diameter can be as small as 1.0 mm or less depending on the condition of the underlying delivery balloon profile. A small crimped outer diameter is especially important if stent delivery is to be attempted without predilation of the target site. When the stent is optimally crimped over the delivery balloon, the surface of the crimped stent is smooth allowing for no snagging of the stent struts during either forward or backward movement through a vessel.

Figure 5A:
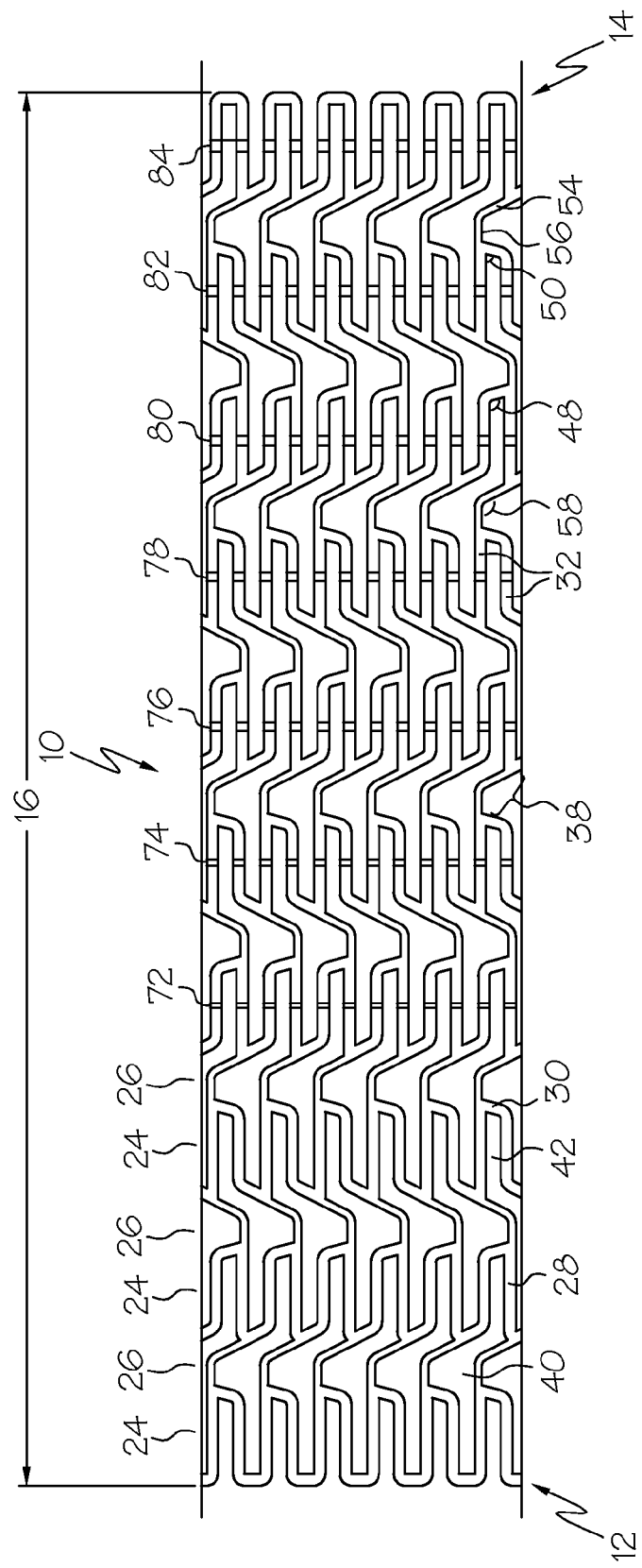
FIG. 5A is a scale drawing of an embodiment of the stent of the present invention with a tapered diameter in its post-expansion mode.
Figure 5B:
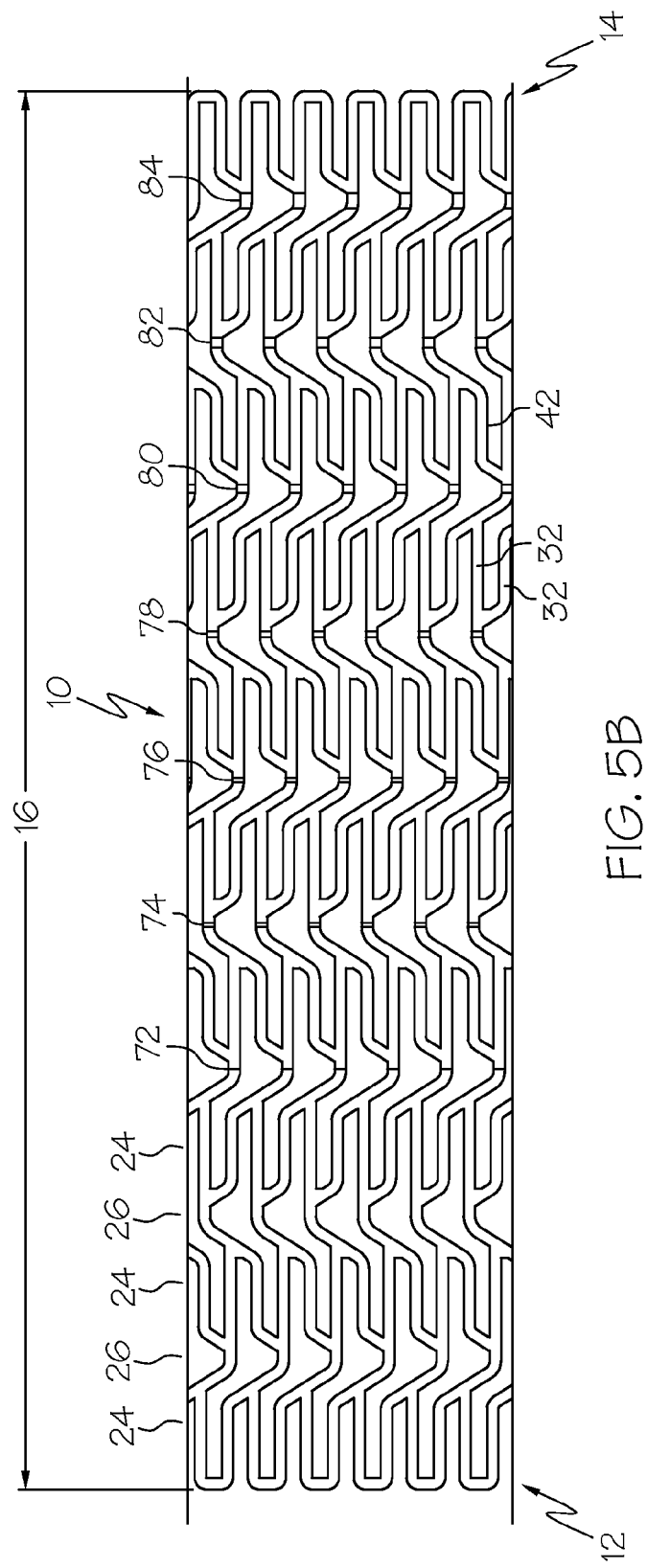
FIG. 5B is a scale drawing of an embodiment of the stent of the present invention, the stent having a tapered diameter in its post-expansion mode.
Figure 5C:
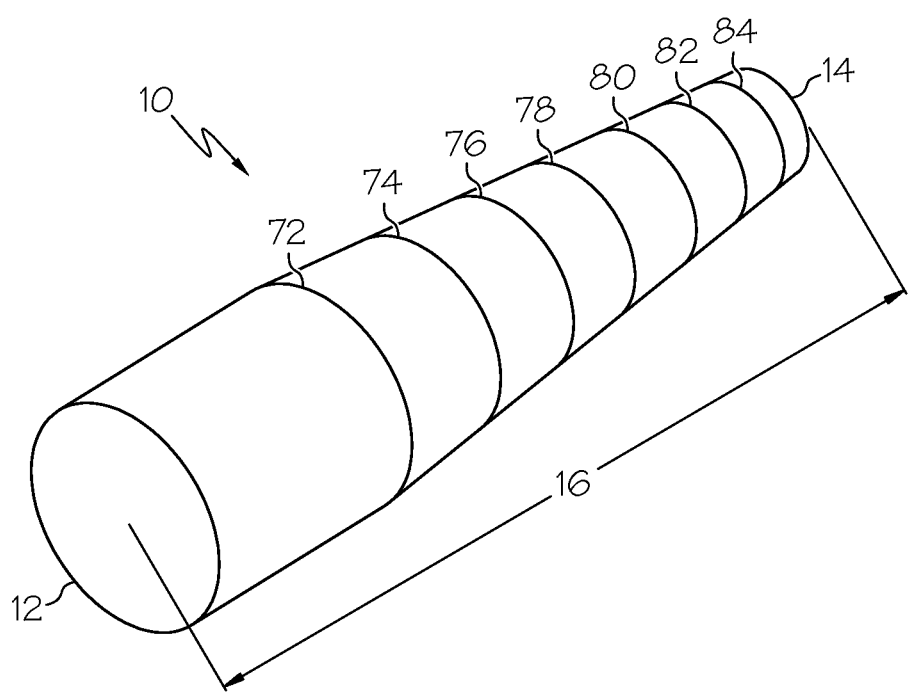
FIG. 5C is a schematic of an embodiment of the stent of the present invention in an expanded state with a tapered diameter.

FIGS. 5A and 5C shows a second embodiment of the present invention in which the stent 10 in its expanded form has a gradual taper from proximal end 12 to distal end 14. The shaded segments 72, 74, 76, 78, 80, 82 and 84 of expansion struts 28 represent regions of expansion struts 28 to be removed. As shown schematically in FIG. 5C, removal of the shaded segments 72, 74, 76, 78, 80, 82 and 84 provides stent 10 with a gradual taper when expanded with distal end 14 having a smaller expanded diameter than proximal end 12. The degree of shortening of the expanded diameter of the stent 10 at a given expansion column 24 will be proportional to the length of the removed segment 72, 74, 76, 78, 80, 82, or 84 at that expansion column 24. In the expanded stent 10 the shortened expansion struts 28 will have a shortened component along the circumference of the stent resulting in a shortened circumference and diameter. The tapered diameter portion can be positioned anywhere along the length of stent 10, and the tapering can be made more or less gradual by removing appropriately larger or smaller portions of the expansion struts 28 in a given expansion column 24.

Tapering is especially important in long stents, longer than 12 mm, since tapering of blood vessels is more pronounced over longer lengths. A long stent with a uniform stent diameter can only be matched to the target vessel diameter over a short region. If the proximal vessel size is matched with the stent diameter, the expanded distal end of the stent will be too large for the natural vessel and may cause an intimal dissection of the distal vessel by stent expansion. On the other hand, if the distal vessel size is matched with the stent diameter, the proximal end of the expanded stent will be too small to set inside the vessel lumen. It is therefore desirable to have a stent with a tapered expanded diameter.

Another way to achieve a tapered expanded stent is to change the stiffness of the stent struts, expansion struts, connecting struts or joining struts such that the stiffness of the struts varies along the length of the stent. The stiffness of the struts can be changed by altering length, width or thickness, adding additional stiffening material, using a chemical or mechanical means to alter the physical properties of the stent material, or applying one or a series of elastic elements about the stent. FIG. 5B shows an embodiment of the present invention where the stiffness of the connecting struts is changed by altering the length of the connecting struts as described above. The shaded segments 72, 74, 76, 78, 80, 82 and 84 of connection struts 38 represent regions of connection struts 38 to be removed in order to provide the tapered configuration described. A stent having this configuration is shown in FIG. 5C in the expanded state.

Along with the use of a tapered diameter stent, a matching tapered balloon catheter would ideally be made for delivery and deployment of the tapered diameter stent. The method of using a tapered matching balloon catheter with a tapered diameter stent is within the scope of the present invention.

Using a tapered balloon to expand a non-tapered stent will also achieve a tapered expanded stent; however, since no metal is removed from the stent, the stent is tapered as a result of incomplete expansion. The stent will therefore have increased metal fraction at the tapered end resulting in increased risk of acute thrombosis. Metal fraction is the proportion of the surface of the expanded stent covered by the stent strut material. Shortening the expansion struts as shown in FIGS. 5A and 5C allows for a tapered expanded stent with substantially constant metal fraction along its length.

Figure 6B:
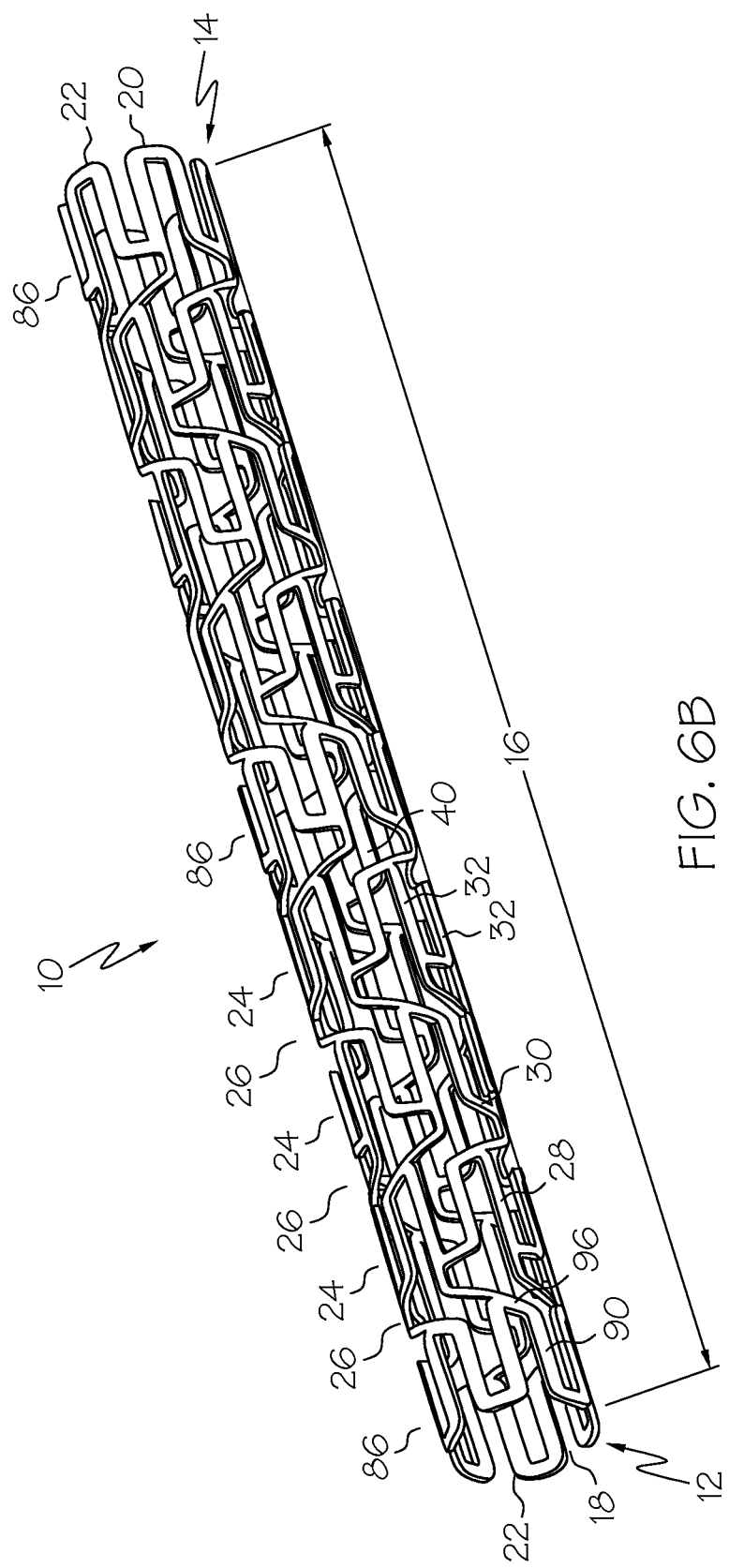
FIG. 6B is a perspective view of the embodiment of FIG. 6A.

A third embodiment of the present invention shown in FIGS. 6A, 6B and 6C has multiple reenforcement expansion columns 86 placed along the length of the stent 10. The reenforcement columns 86 are placed along the stent length to provide additional localized radial strength and rigidity to stent 10. Additional strength and rigidity are especially important at the ends of the stent to prevent deformation of the stent both during delivery and after placement. During delivery the stent ends can catch on the vessel wall possibly deforming the unexpanded stent and altering its expansion characteristics. After the stent has been placed it is important that the stent ends are rigid so that they set firmly against the vessel wall; otherwise, during a subsequent catheter procedure, the catheter or guidewire can catch on the stent ends pulling the stent away from the vessel wall and possibly damaging and/or blocking the vessel.

The specific variation of the third embodiment of stent 10 depicted in FIGS. 6A, 6B and 6C has a length 16 of 20.70 mm and an uncrimped and unexpanded circumference 88 of 5.26 mm. The stent 10 consists of six expansion columns 24 and three reenforcement expansion columns 86, each consisting respectively of twelve expansion struts 28 or reenforcement expansion struts 90. The reenforcement expansion columns 86 are positioned one at either end, and one along the length of the stent 10.

The expansion strut width 62 is 0.15 mm, reenforcement expansion strut width 92 is 0.20 mm, and the connecting strut width 66 is 0.10 mm. The narrow angle 48 formed by joining strut 30 and expansion strut 28 is 75 degrees, and the narrow angle 94 formed by reenforcement joining strut 96 and reenforcement expansion strut 90 is 60 degrees.

Other arrangements of reenforcement expansion columns 86, such as providing reenforcement expansion columns 86 only on the ends of the stent, only on one end, or at multiple locations throughout the length of the stent can also be used and fall within the scope of the present invention. A taper can also be programmed into the reenforced stent 10 by shortening expansion struts 28 and reenforcement expansion struts 90 in appropriate expansion columns 24 and 86.

Figure 7A:
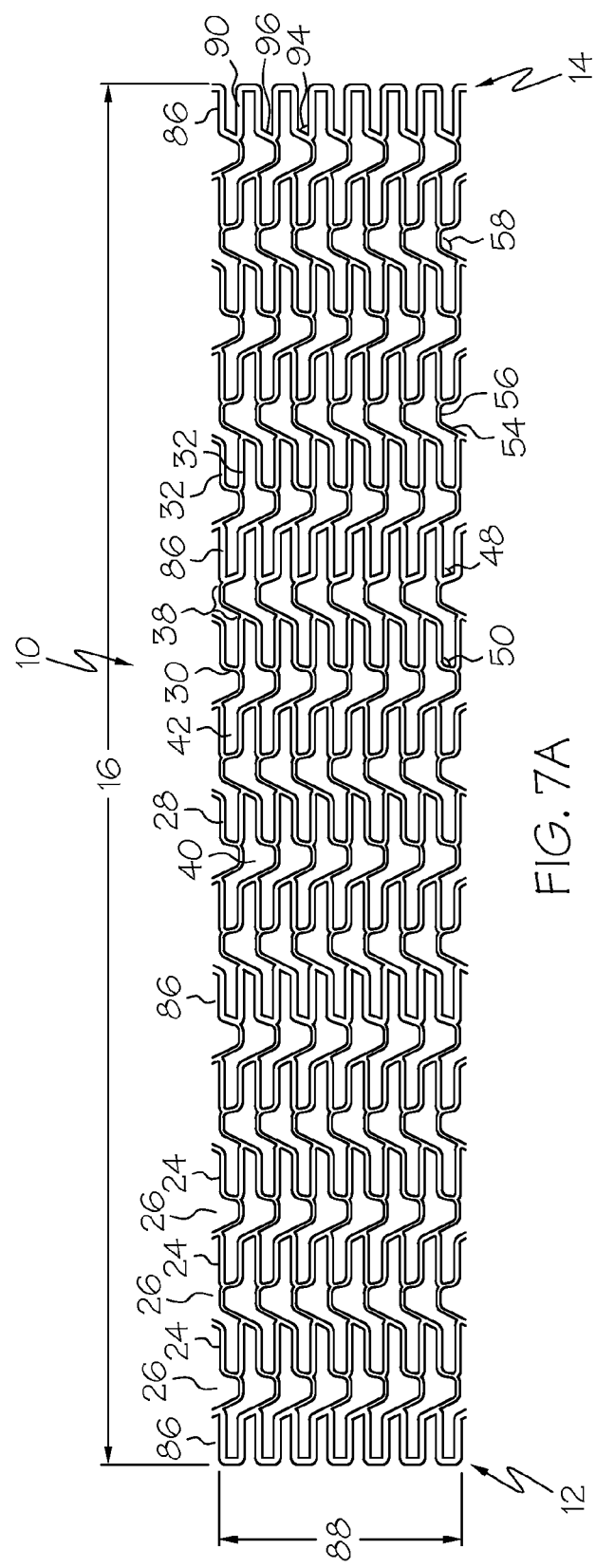
FIG. 7A is a scale drawing of an embodiment of the stent of the present invention including relief notches at strut joints to increase flexibility of the joints.
Figure 7B:
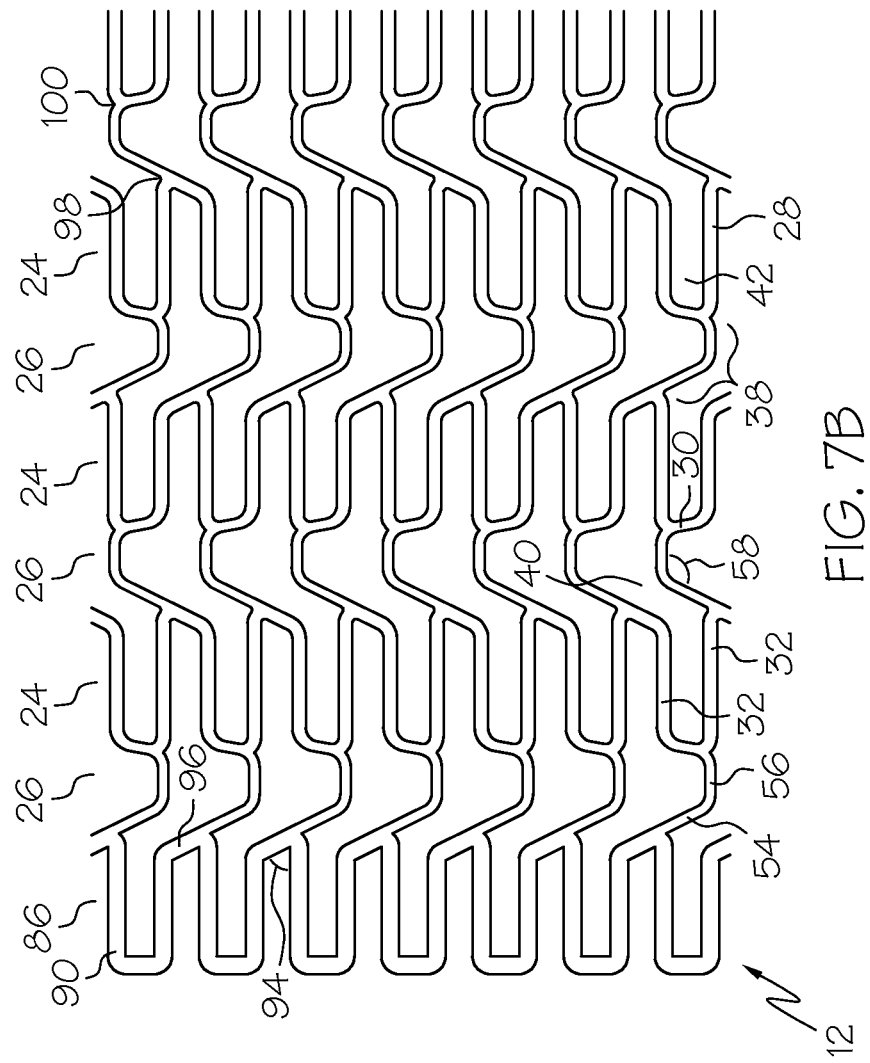
FIG. 7B is an enlarged region of the embodiment of FIG. 7A.
Figure 7C:
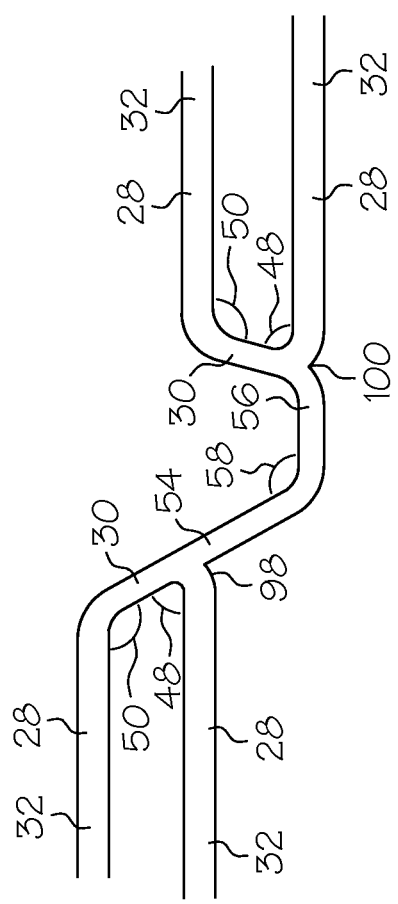
FIG. 7C is an enlarged view of a single connecting strut joining two expansion strut pairs in accordance with the embodiment of FIG. 7A.

A fourth embodiment of the present invention, shown in the FIGS. 7A, 7B and 7C, is similar to the third embodiment but has the added feature of relief notches 98 and 100. A relief notch is a notch where metal has been removed from a strut, usually at a joint where multiple struts are connected. Relief notches increase flexibility of a strut or joint by creating a thinned, narrow region along the strut or joint. Relief notch 98 is formed at the joint formed between first linear section 54 of connecting strut 38 and expansion strut 28. Relief notch 100 is formed at the joint between second linear section 56 of connecting strut 38 and expansion strut 28. The positioning of the relief notches gives added flexibility to the unexpanded stent and prevents warping at the joints when the stent is expanded. This results in a smooth surface modulation to the expanded stent frame. Relief notches can be placed at other joints and can be included in any of the previously mentioned embodiments.

Figure 8A:
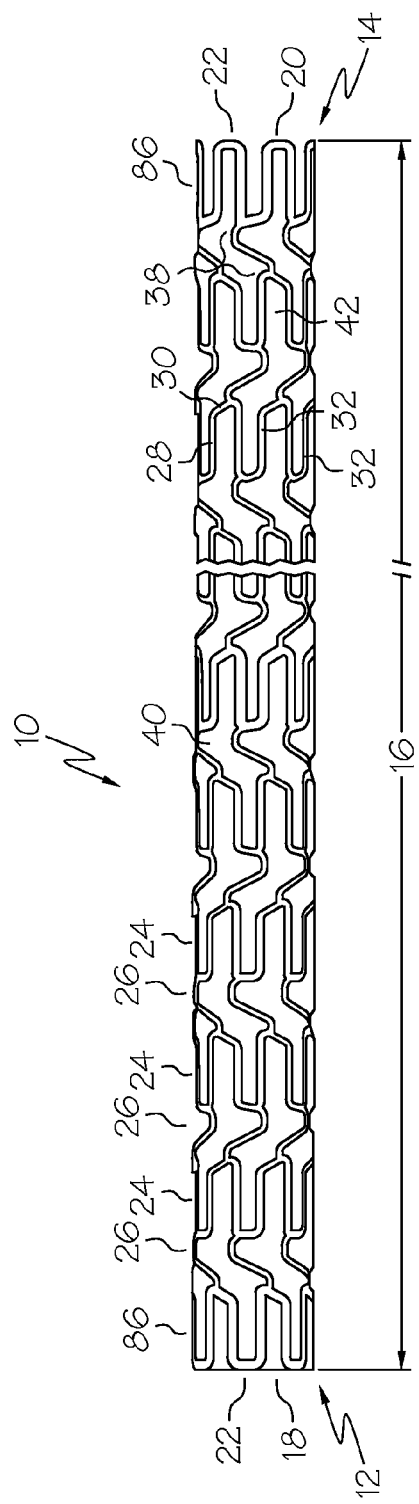
FIG. 8A is a side elevation view of an embodiment of the stent of the present invention.
Figure 8B:
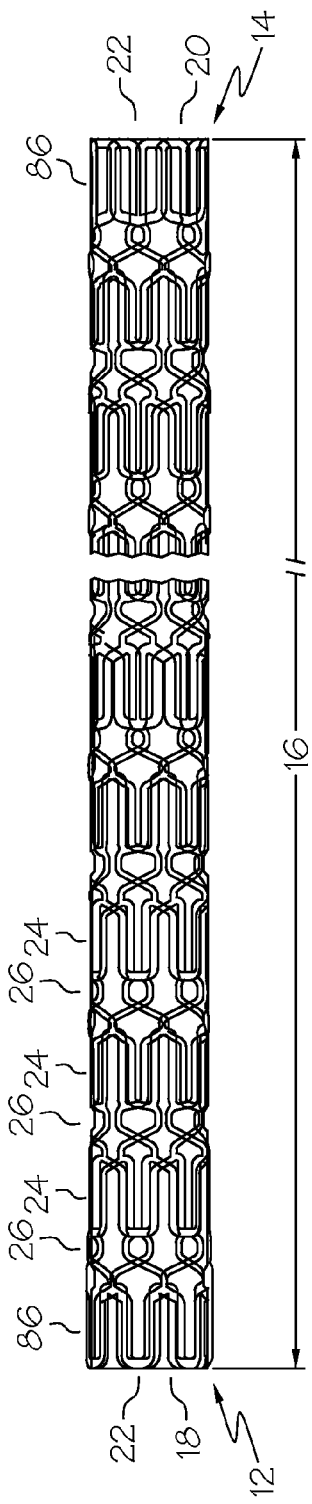
FIG. 8B is a side elevation view of an embodiment of the stent of the present invention, shown as if the stent struts and space there between were transparent.

FIGS. 8A and 8B show a side elevation view of a variation of the fifth embodiment of the stent of the present invention. In this embodiment a four piece slanted connecting strut 38 is used to couple the corner of an expansion strut pair 32 in one expansion column 24 to the joining strut 30 of a circumferentially offset expansion strut pair 32 in an adjacent expansion column 24. The expansion struts 28, joining struts 30, expansion columns 24, reenforcement expansion struts 90, reenforcement joining struts 96, and reenforcement expansion columns 86 are substantially similar to the fourth embodiment of FIG. 6A. Connecting struts 38 in connecting strut columns 26, however, have an altered geometry and connectivity; described in more detail below.

FIG. 8A shows only the stent struts on the front half of the stent surface. The stent struts on the rear half of the stent surface are not shown. The stent appears as it would if the stent struts and space there between were opaque. FIG. 8B shows all stent struts from both the front and rear halves. The stent appears as it would if the stent struts and the space there between were transparent.

A first variation of a fifth embodiment of the present invention, shown in FIG. 8C consists of a stent 10 with twelve expansion columns 24, four reenforcement expansion columns 86, and fifteen connecting strut columns 26. In this variation, the stent 10 has a length 16 of 31.96 mm, and an unexpanded circumference 88 of 5.26 mm.

Figure 8D:
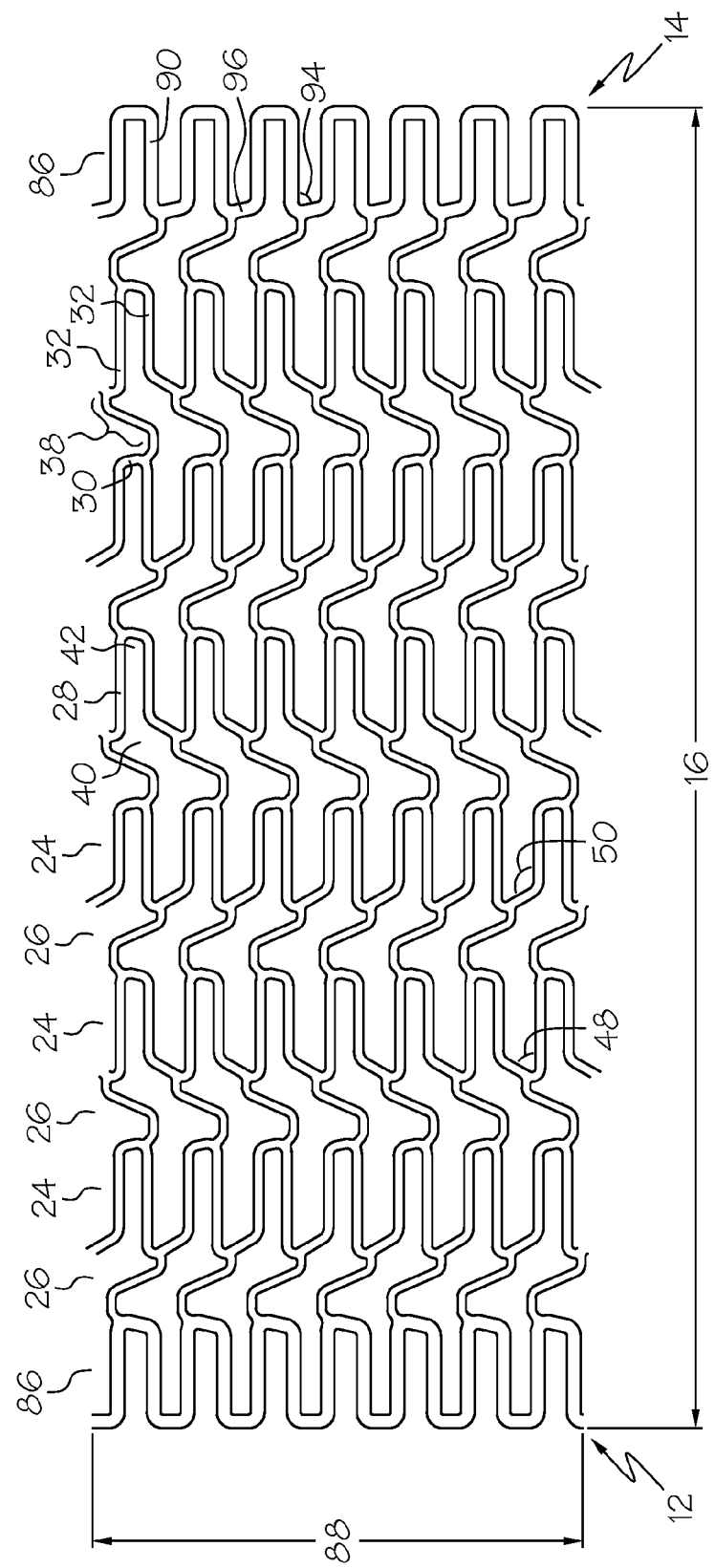
FIG. 8D is a variation of the embodiment of the stent of FIG. 8C.
Figure 8F:
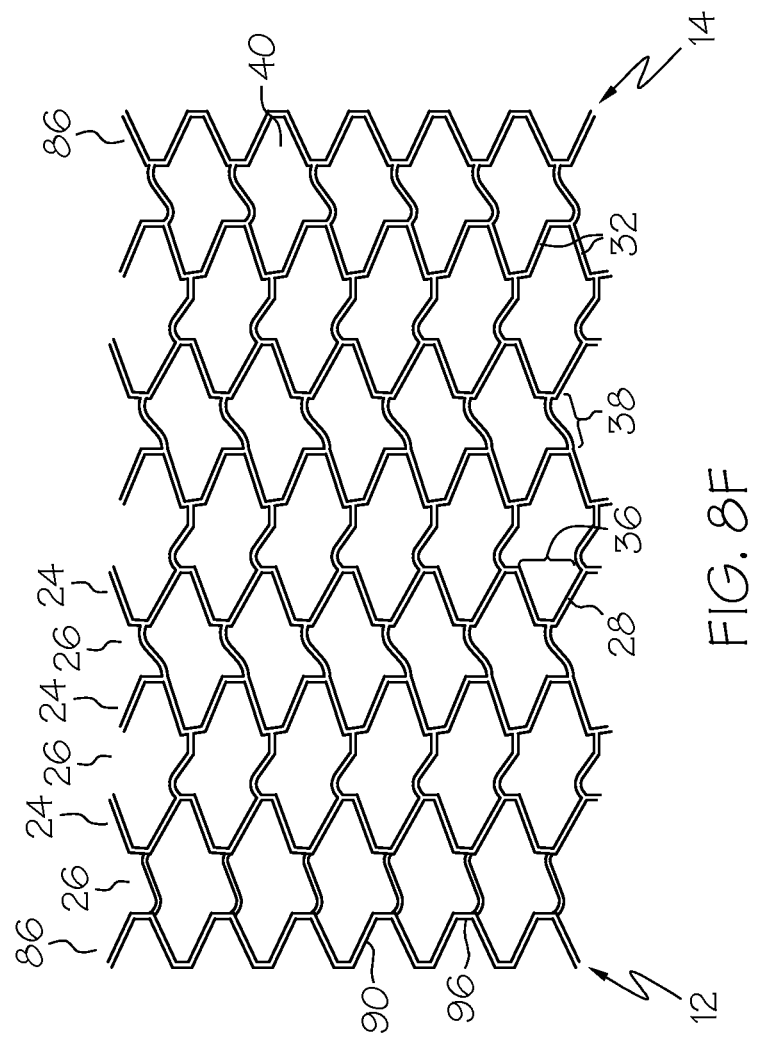
FIG. 8F is a drawing illustrating the post-expansion mode of the stent of the embodiment of FIG. 8D of the present invention.
Figure 8G:
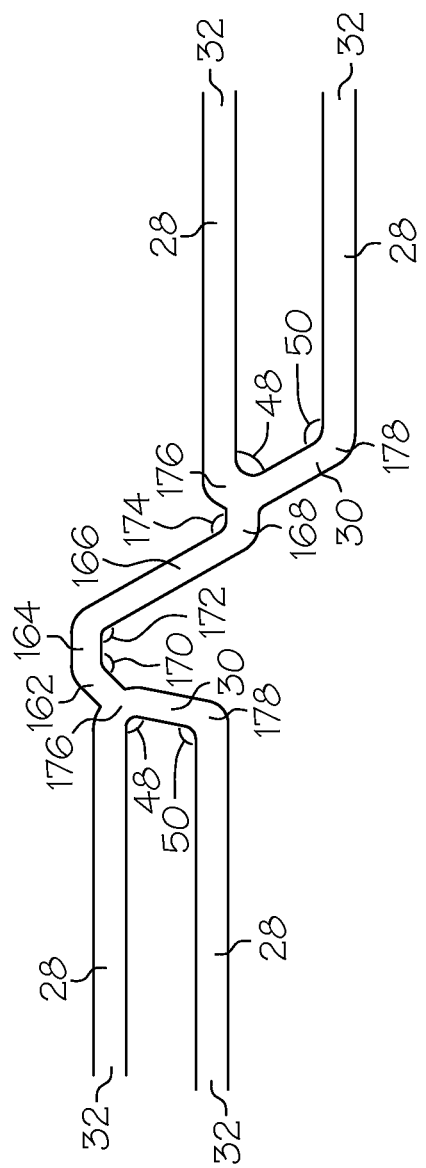
FIG. 8G is an enlarged view of a single connecting strut joining two expansion strut pairs in accordance with an embodiment of the present invention.

Connecting struts 38 shown in an enlarged view in FIG. 8G are made up of four linear sections, a proximal end section 162, first and second intermediate sections 164 and 166 respectively and a distal end section 168 forming three slant angles 170, 172 and 174. The proximal end of proximal section 162 is attached to a corner 176 of an expansion strut pair 32 of an expansion column 24. Corner 176 is formed where joining strut 30 makes narrow angle 48 with expansion strut 28. A second corner 178 of expansion strut 32 is formed where joining strut 30 makes wide angle 50 with expansion strut 28. Corners 176 and 178 can have an angular shape formed by joining linear expansion struts 28 and joining struts 30, or preferably corners 176 and 178 are rounded to remove sharp edges and provide increased flexibility. Additionally rounded corners provide stent 10 with greater expandability and reduce stress in the stent strut material at the corners in the expanded stent.

Proximal end section 162 of connecting strut 38 extends from corner 176 and is attached at its distal end to first intermediate section 164 forming slant angle 170. First intermediate section 164 extends from proximal end section 162 such that first intermediate section 164 is parallel to expansion struts 28 and is connected at its distal end to the proximal end of second intermediate section 166 forming slant angle 172.

Second intermediate section 166 extends in a slanted orientation relative to the longitudinal axis of stent 10, extending both longitudinally along and circumferentially about stent 10. Preferably, second intermediate section 166 is parallel to joining strut 30 of the circumferentially offset expansion strut pair 32 in adjacent expansion column 24.

Second intermediate section 166 attaches at its distal end to the proximal end of distal end section 168 forming slant angle 174. Distal end section 168 extends from second intermediate section 166 attaching at its distal end to joining strut 30 of circumferentially offset expansion strut pair 32 of adjacent expansion column 24. The attachment is at a point intermediate corners 176 and 178, where joining strut 30 forms narrow angle 48 and wide angle 50 respectively with expansion struts 28.

The connection point of distal end section 168 to joining strut 30 is closer to corner 176 than corner 178. Preferably the connection point is one to two or more expansion strut widths from corner 176. Offsetting the connection point of distal end section 168 to joining strut 30 from corner 176 to a point intermediate corner 176 and corner 178 reduces warping of the expanded stent 10, resulting in a smooth surface modulation and reduced risk of thrombosis. Additionally, this design provides a longer total straightened length of connecting strut 38, which further reduces foreshortening of stent 10 during expansion.

A second variation of a fifth embodiment of the present invention, shown in an unexpanded form in FIGS. 8D, 8E and in an expanded form in FIG. 8F consists of a stent 10 with six expansion columns 24, two reenforcement expansion columns 86, and seven connecting strut columns 26. In this variation, the stent 10 has a length 16 of 15.04 mm, and an unexpanded circumference 88 of 5.26 mm. The stent design 10 is substantially similar to the design of the first variation of the fifth embodiment of FIG. 8C with a reduced number of expansion columns, reenforcement expansion columns, and connecting strut columns.

FIG. 8F illustrates a portion of the expanded stent 10 of the second variation of the fifth embodiment. After expansion of stent 10 by balloon or other means, the expansion struts 28 are spread apart circumferentially, increasing the separation at the open end 36 of expansion strut pairs 32 resulting in an increase in the circumference of the stent 10. The spreading of the expansion struts 28 causes a longitudinal shortening of the expansion columns 24, which is compensated by a straightening of the connecting struts 38. During the expansion process, the slant angles 170, 172 and 174 widen straightening the connection struts 38, and causing an increase in the separation distance between adjacent expansion columns 24. The asymmetrical interlocking cell geometry of the expanded stent is illustrated in FIG. 8F.

FIGS. 9A, 9B, 9C, 9D, 9E, 9F and 9G illustrate a sixth embodiment of the stent of the present invention. In this embodiment a three piece slanted connecting strut 38 is used to couple the joining strut 30 of an expansion strut pair 32 in one expansion column 24 to the joining strut 30 of a circumferentially offset expansion strut pair 32 in an adjacent expansion column 24. The joints between segments of connecting strut 38 are curved forming a smooth rounded shape. The expansion struts 28, joining struts 30, expansion columns 24, reenforcement expansion struts 90, reenforcement joining struts 96, and reenforcement expansion columns 86 are substantially similar to the fourth embodiment of FIG. 8A. Connecting struts 38 in connecting strut columns 26, however, have an altered geometry and connectivity, described in more detail below.

Figure 9A:
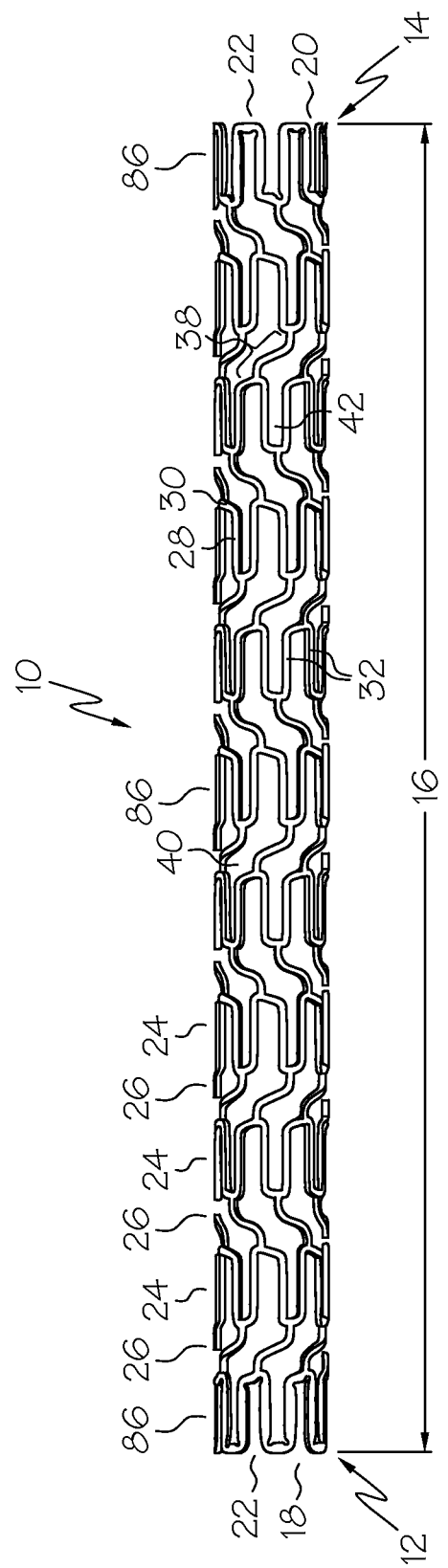
FIG. 9A is a side elevation view of an embodiment of the stent of the present invention.
Figure 9B:
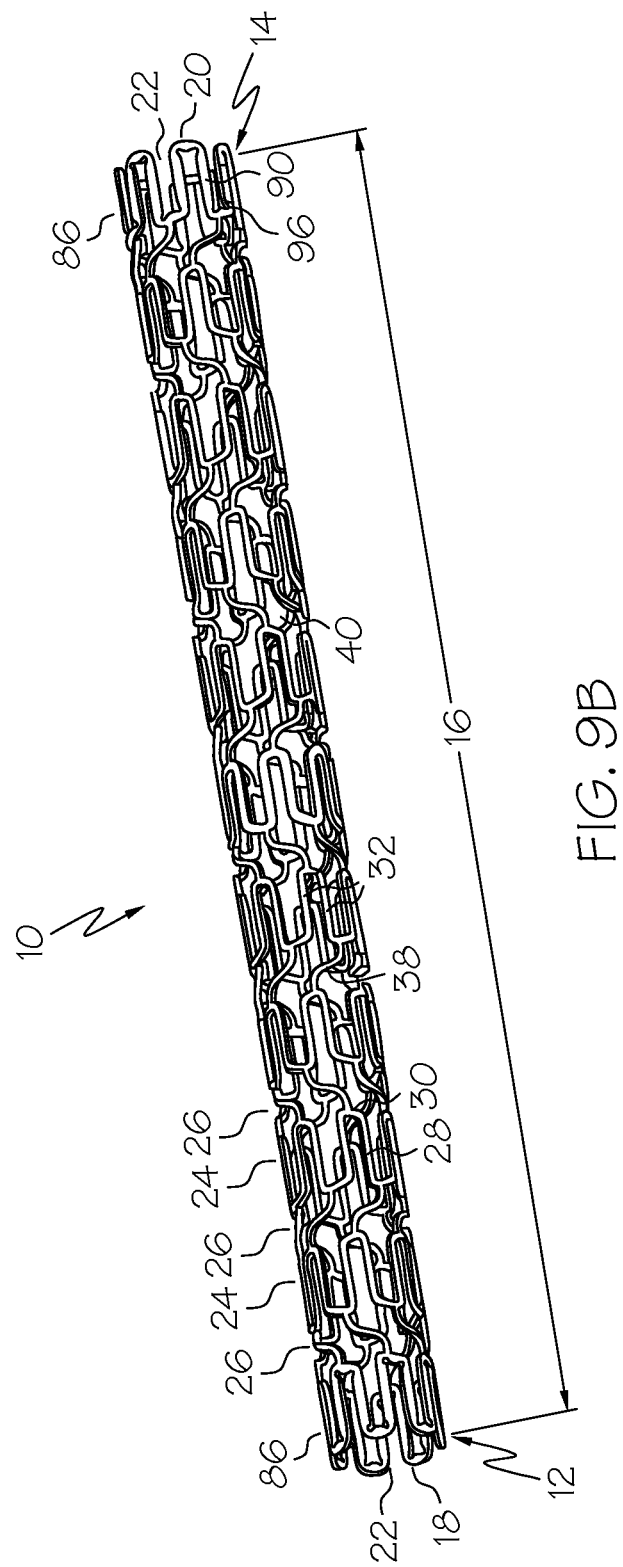
FIG. 9B is a perspective view of the embodiment of FIG. 9A.
Figure 9C:
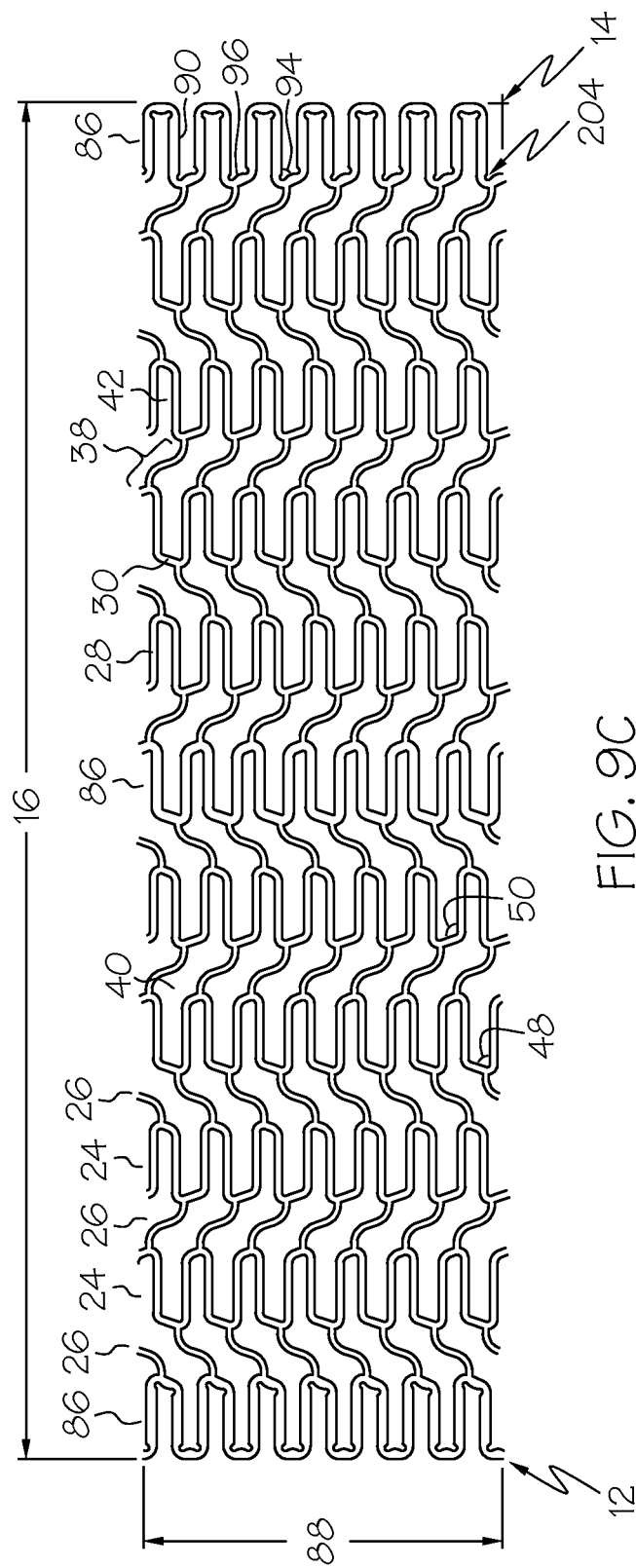
FIG. 9C is a scale drawing of the embodiment of FIG. 9A.

A first variation of a sixth embodiment of the present invention, shown in FIGS. 9A, 9B and 9C consists of a stent 10 with eight expansion columns 24, three reenforcement expansion columns 86, and ten connecting strut columns 26. In this variation, the stent 10 has a length 16 of 20.32 mm.

Relief notches 204 are utilized at the joints between reenforcement expansion struts 90 and reenforcement joining struts 96 in the reenforcement expansion columns 86 at the stent proximal end 12 and distal end 14. Relief notches 204 reduce the width of the joints between reenforcement expansion struts 90 and reenforcement joining struts 96, which reduces stress in the metal at the joints during and after expansion of the stent. Relief notches 204 are particularly important at the stent ends since the stent ends are especially susceptible to warping during and after expansion. Preferably relief notches 204 reduce the joint widths, such that the joint widths are substantially the same as the thickness of stent wall 46 (see FIGS. 1B and 1C).

Figure 9D:
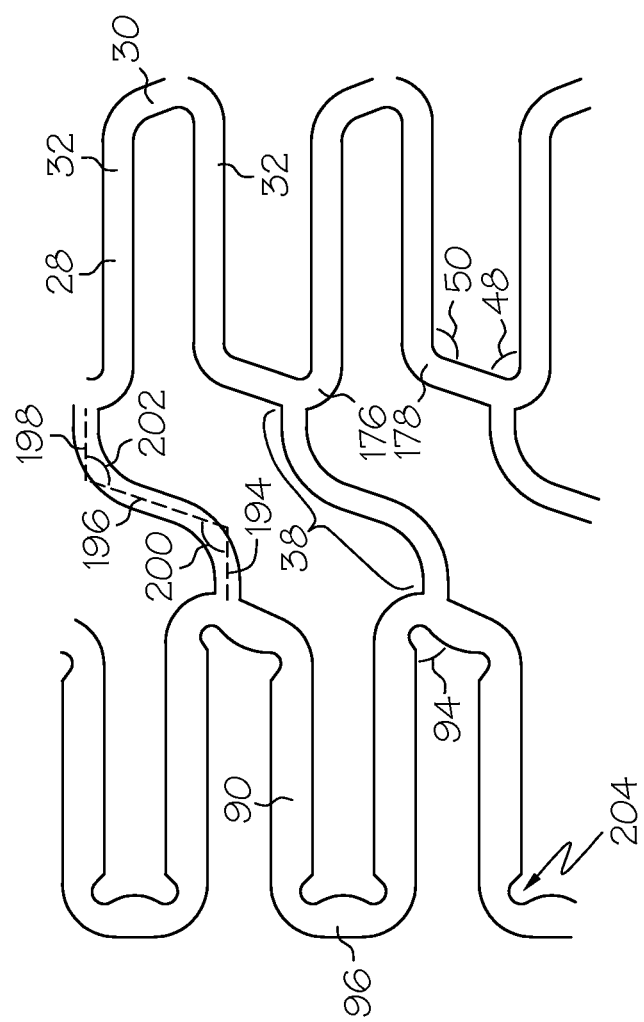
FIG. 9D is an enlarged region of the drawing of FIG. 9C.

Connecting struts 38 shown in an enlarged view in FIG. 9D are made up of three linear sections, a proximal end section 194, an intermediate section 196 and a distal end section 198 forming two slant angles 200, 202. The connecting struts 38 have wide radii of curvature at the joints between connecting strut sections 194, 196 and 198. The shape of connecting strut 38 is thus curved or wavy rather than jagged and angular. The slant angles 200 and 202 are defined by linearly extrapolating proximal end section 194, intermediate section 196 and distal end section 198, as shown by the dotted lines in FIG. 9D.

Figure 9E:
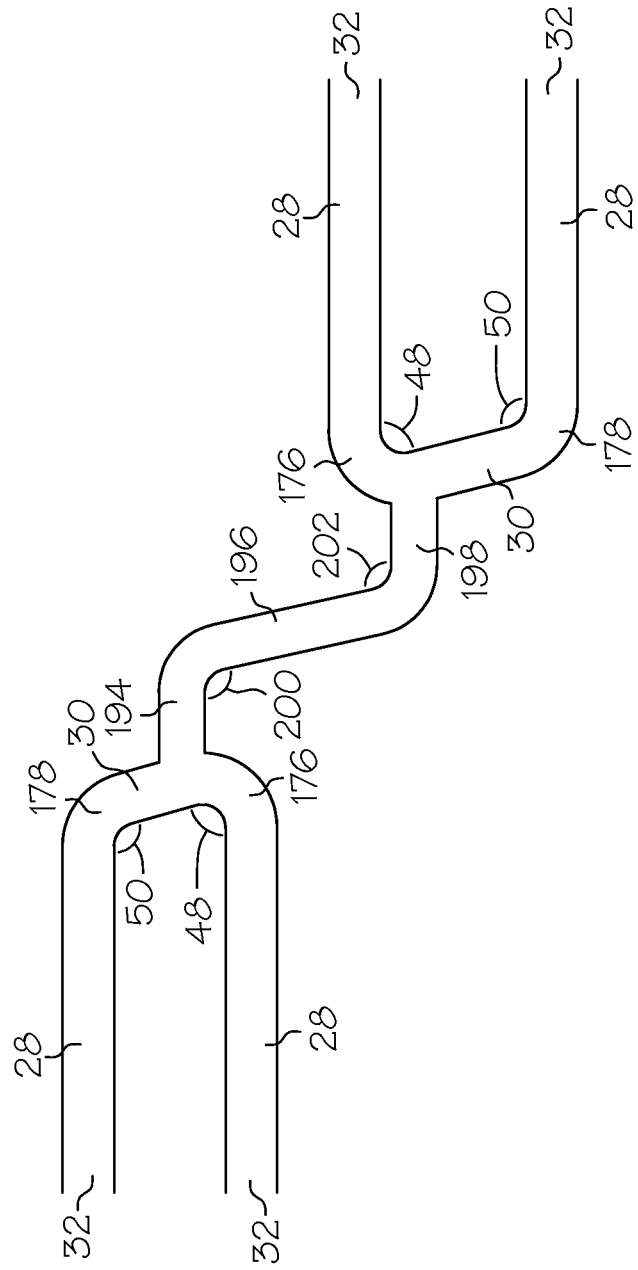
FIG. 9E is a scale drawing of an embodiment of the stent of the present invention.

FIG. 9E shows a variation of the connecting strut design of the sixth embodiment of the present invention. The connecting strut 38 of FIG. 9E has smaller radii of curvature at the joints between proximal end section 194, intermediate section 196 and distal end section 198. Connecting strut 38 of FIG. 9E is thus more jagged and angular than that of FIG. 9D.

Referring to the connecting struts 38 of FIGS. 9D and 9E, the proximal end of proximal section 194 is attached to joining strut 30 of expansion strut pair 32 intermediate corners 176 and 178. Proximal end section 194 of connecting strut 38 extends from joining strut 30 and is attached at its distal end to intermediate section 196 forming slant angle 200. Intermediate section 196 extends from proximal end section 194 in a slanted orientation relative to the longitudinal axis of stent 10, extending both longitudinally along and circumferentially about stent 10. Intermediate section 196 is preferably parallel to joining struts 30 of coupled expansion strut pairs 32.

Intermediate section 196 is connected at its distal end to the proximal end of distal end section 198 forming slant angle 202. Distal end section 198 extends from second intermediate section 196 attaching at its distal end to joining strut 30 of circumferentially offset expansion strut pair 32 of adjacent expansion column 24. The attachment is at a point intermediate corners 176 and 178, where joining strut 30 forms narrow angle 48 and wide angle 50 respectively with expansion struts 28.

The connection point of proximal end section 194 and distal end section 198 to joining struts 30 is closer to corner 176 than corner 178. Preferably the connection point is one to two or more expansion strut widths from corner 176. Offsetting the connection point of distal end section 198 to joining strut 30 from corner 176 to a point intermediate corner 176 and corner 178 reduces warping of the expanded stent 10, resulting in a smooth surface modulation and reduced risk of thrombosis. Additionally, this design provides a longer total straightened length of connecting strut 38, which further reduces foreshortening of stent 10 during expansion.

The connecting strut 38 of the sixth embodiment has one hundred and eighty degree rotational symmetry about its center. The symmetry of the connecting strut 38 does not, however, result in a symmetrical cell space as the width of loop slots 42 connected in each cell space are different. Adjacent loop slots 42 in each expansion column have alternating narrow and wide widths, preserving the asymmetry of the cell spaces. Introduction of one or many symmetrical cell spaces can be achieved in this design e.g. by providing uniform loop slot width to loop slots in adjacent expansion columns 24 contained in the same cell space. Additionally completely non-uniform cell space patterns utilizing symmetric or asymmetric cell spaces can be achieved e.g. by providing non-uniform variations in the widths of loop slots 42.

Figure 9F:
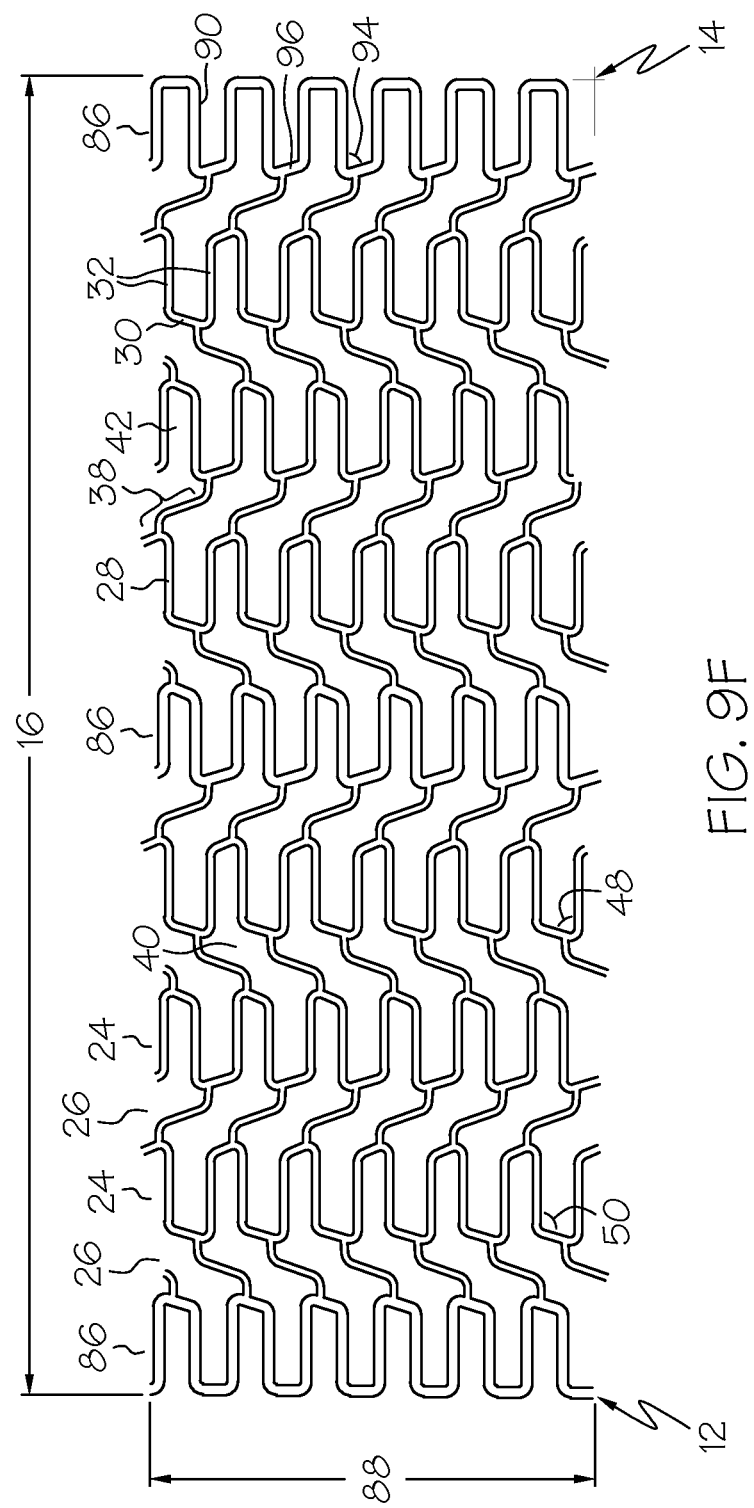
FIG. 9F is a scale drawing of an embodiment of the stent of the present invention.

A second variation of a sixth embodiment of the present invention shown in an unexpanded form in FIGS. 9F consists of a stent 10 with six 10 expansion columns 24, three reenforcement expansion columns 86, and eight connecting strut columns 26. In this variation, the stent 10 has a length 16 of 16.00 mm, and an unexpanded circumference 88 of 5.26 mm. The stent design 10 is substantially similar to the design of the first variation of the sixth embodiment of FIGS. 9A, 9B and 9C with a reduced number of expansion columns 24 and connecting strut columns 26.

A third variation of a sixth embodiment of the present invention, shown in an unexpanded form in FIG. 9F consists of a stent 10 with twelve expansion columns 24, four reenforcement expansion columns 86, and fifteen connecting strut columns 26. In this variation, the stent 10 has a length 16 of 30.01 mm, and an unexpanded circumference 88 of 5.26 mm. The stent design 10 is substantially similar to the design of the first variation of the sixth embodiment of FIGS. 9A, 9B and 9C with an increased number of expansion columns 24 reenforcement expansion columns 86 and connecting strut columns 26.

Figure 10F:
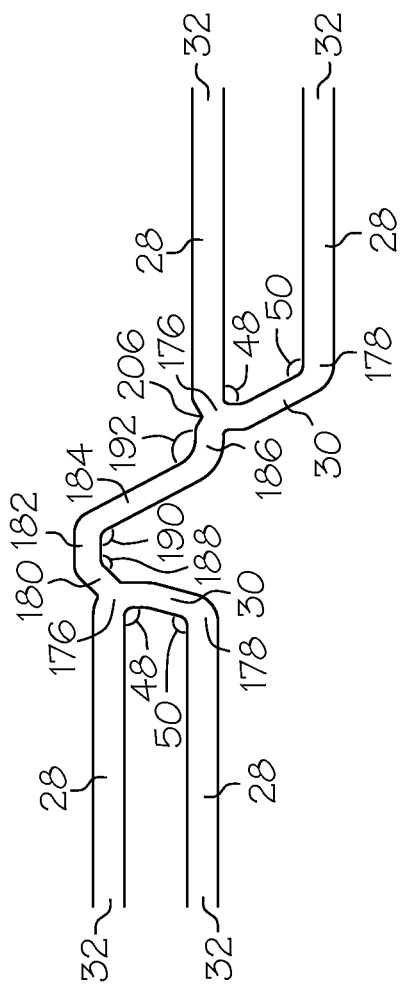
FIG. 10F is a drawing of an alternate geometry of connecting struts and joining struts in accord with the present invention.

FIGS. 10A, 10B, 10C, 10D, 10E and 10F illustrate some examples of alternate connecting strut designs which can be used in any of the previously discussed embodiments. FIG. 10A shows a rounded loop connecting strut 38 which joins two circumferentially offset expansion strut pairs 32 in adjacent expansion columns. Expansion struts 28 in each expansion strut pair 32 are joined by a joining strut 30. Joining struts 30 are slanted such as to form a narrow angle 48 and a wide angle 50 with the expansion struts 28 they connect. The rounded loop connecting strut 38 connects expansion struts 28 at the point where narrow angle 48 is formed between expansion struts 28 and joining struts 30. The slopes of the rounded connecting strut 38 at its proximal end 102 and distal end 104 substantially match the slopes of the joining struts 30 connecting the pairs of expansion struts 28. The rounded loop connecting strut 38 thus blends smoothly into the joining struts 30. Additionally the rounded loop connecting strut 38 has a first radius of curvature 106 and a second radius of curvature 108.

In the design of FIG. 10B a rounded loop connecting strut 38 joins two circumferentially offset expansion strut pairs 32 in adjacent expansion columns. Expansion struts 28 in each expansion strut pair 32 are joined by a joining strut 30. Joining struts 30 are at right angles to the expansion struts 28 they connect. The rounded loop connecting strut 38 connects to expansion struts 28 at the same point as joining struts 30. The rounded connecting strut 38 has a first radius of curvature 106 and a second radius of curvature 108 such that it connects circumferentially offset expansion strut pairs 32.

In the design of FIG. 10C connecting strut 38 joins two circumferentially offset expansion strut pairs 32 in adjacent expansion columns. Expansion struts 28 in each expansion strut pair 32 are joined by a joining strut 30. Joining struts 30 are slanted such as to form a narrow angle 48 and a wide angle 50 with the expansion struts 28 they connect. The connecting strut 38 connects expansion struts 28 at the point where narrow angle 48 is formed between expansion strut 28 and joining strut 30.

The connecting strut 38 is made up of three linear sections 110, 112, and 114 forming two slant angles 116 and 118. The proximal end of section 110 is attached to expansion strut 28 at the point where joining strut 30 forms narrow angle 48 with expansion strut 28. Section 110 extends substantially collinear to joining strut 30 and is attached at its distal end to intermediate section 112 forming slant angle 116. Intermediate section 112 extends at an angle to section 110 such that intermediate section 112 is substantially parallel to expansion struts 28 and is connected at its distal end to the proximal end of distal section 114 forming slant angle 118. Distal section 114 extends at an angle such that it is substantially collinear to joining strut 30 of the adjacent expansion strut pair 32. Distal section 114 attaches at its distal end to expansion strut 28 of the adjacent expansion strut pair 32, at the point where joining strut 30 forms narrow angle 48 with expansion strut 28.

In the design of FIGS. 10D and 10E a connecting strut 38 joins two circumferentially offset expansion strut pairs 32 in adjacent expansion columns. Expansion struts 28 in each expansion strut pair 32 are joined by a joining strut 30. Joining struts 30 are at right angles to the expansion struts 28 they connect. The connecting strut 38 connects to expansion struts 28 at the same point as joining struts 30.

The connecting struts 38 of FIGS. 10D and 10E are made up of multiple connecting strut sections connected end to end to form a jagged connecting strut 38 with multiple slant angles, coupling expansion strut pair 32 to adjacent expansion strut pair 32. The connecting strut of FIG. 10D is made up of three connecting strut sections, a proximal section 120, an intermediate section 122 and a distal section 124 defining two slant angles 126 and 128, while the connecting strut of FIG. 10E consists of four connecting strut sections, a proximal section 130, intermediate sections 132 and 134, and a distal section 136 defining three slant angles 138, 140 and 142. In addition, connecting strut section 134 can be modified by replacing connecting strut section 136 by the dotted connecting strut section 144 to give another possible geometry of connecting struts 38.

In the design of FIG. 10F connecting strut 38 joins two circumferentially offset expansion strut pairs 32 in adjacent expansion columns. Expansion struts 28 in each expansion strut pair 32 are joined by a joining strut 30. Joining struts 30 are slanted such as to form a narrow angle 48 and a wide angle 50 with the expansion struts 28 they connect.

Connecting strut 38 is made up of four linear sections, a proximal end section 180, first and second intermediate sections 182 and 184 respectively and a distal end section 186 forming three slant angles 188, 190 and 192. The proximal end of section 180 is attached to corner 176 at the point where joining strut 30 forms narrow angle 48 with expansion strut 28. Proximal end section 180 extends at an angle to joining strut 30 and is attached at its distal end to first intermediate section 182 forming slant angle 188. First intermediate section 182 extends at an angle to proximal end section 180 such that first intermediate section 182 is substantially parallel to expansion struts 28 and is connected at its distal end to the proximal end of second intermediate section 184 forming slant angle 190. Second intermediate section 184 is substantially longer than the first intermediate section 182. Second intermediate section 184 extends at an angle such that it is substantially collinear to joining strut 30 of the adjacent expansion strut pair 32. Second intermediate section 184 attaches at its distal end to the proximal end of distal end section 186 forming slant angle 192. Distal end section 186 extends in a slightly sloping orientation relative to expansion struts 28, attaching to corner 176 of expansion strut pair 32 where joining strut 30 forms narrow angle 48 with expansion strut 28. Relief notches 206 are formed at the joint between distal end segment 186 of connecting strut 38 and corner 176 of expansion strut pair 32 to increase flexibility of the unexpanded stent and prevent warping when the stent is expanded.

One skilled in the art will recognize that there are many possible arrangements of connecting struts and joining struts consistent with the present invention; the above examples are not intended to be an exhaustive list. In particular, it is noted that (a) connecting strut sections need not be linear but may contain one or many radii of curvature, (b) connecting strut sections may each have a different longitudinal axis, (c) the joint between connecting strut sections need not be jagged or sharp, but rather can be smooth containing one or multiple radii of curvature, and (d) relief notches may be present at any of the strut joints.

The stent of the present invention is ideally suited for application in coronary vessels although versatility in the stent design allows for applications in non-coronary vessels, the aorta, and nonvascular tubular body organs.

Typical coronary vascular stents have expanded diameters that range from 2.5 to 5.0 mm. However, a stent with high radial strength and fatigue tolerance that expands to a 5.0 mm diameter may have unacceptably high stent metal fraction when used in smaller diameter vessels. If the stent metal fraction is high, the chances of acute thrombosis and restenosis potential will increase. Even with the same metal fraction a smaller caliber vessel is more likely than a larger one to have a high rate of thrombosis. It is, therefore, preferred to have at least two different categories of stents for coronary application, for example, small vessels stents for use in vessels with diameters from 2.5 mm to 3.0 mm, and large vessel stents for use in vessels with diameters from 3.0 mm to 5.0 mm. Thus, both small vessels and large vessels when treated with the appropriate sized stent will contain stents of similar idealized metal fraction.

The stent of the present invention can be made using a CAM-driven laser cutting system to cut the stent pattern from a stainless steel tube. The rough-cut stent is preferably electro-polished to remove surface imperfections and sharp edges. Other methods of fabricating the stent can also be used such as EDM, photo-electric etching technology, or other methods. Any suitable material can be used for the stent including other metals and polymers so long as they provide the essential structural strength, flexibility, biocompatibility and expandability.

The stent is typically at least partially plated with a radiopaque metal, such as gold, platinum, tantalum or other suitable metal. It is preferred to plate only both ends of the stent by localized plating; however, the entire stent or other regions can also be plated. When plating both ends, one to three or more expansion columns on each end of the stent are plated to mark the ends of the stent so they can be identified under fluoroscopy during the-stenting procedure. By plating the stent only at the ends, interference of the radiopaque plating material with performance characteristics or surface modulation of the stent frame is minimized. Additionally the amount of plating material required is reduced, lowering the material cost of the stent.

After plating, the stent is cleaned, typically with detergent, saline and ultrasonic means that are well-known in the art. The stents are then inspected for quality control, assembled with the delivery balloon catheter, and properly packaged, labeled, and sterilized.

Figure 11:
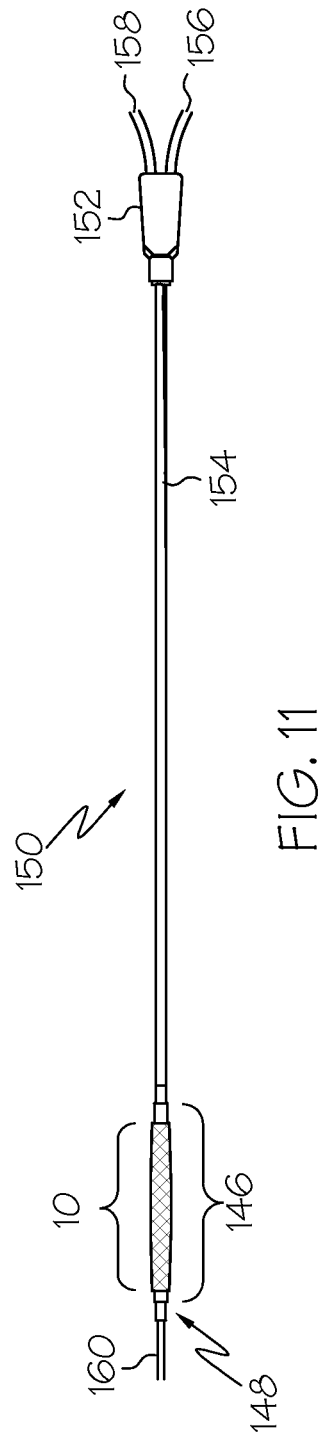
FIG. 11 is a delivery balloon catheter, illustrating a method of deliver of a stent in accord with the present invention.

Stent 10 can be marketed as stand alone or as a pre-mounted delivery balloon catheter assembly as shown in FIG. 11. Referring to FIG. 11, the stent 10 is crimped over a folded balloon 146 at the distal end 148 of a delivery balloon catheter assembly 150. The assembly 150 includes a proximal end adapter 152, a catheter shaft 154, a balloon channel 156, a guidewire channel 158, a balloon 146, and a guidewire 160. Balloon 146 can be tapered, curved, or both tapered and curved from a proximal end to a distal end in the expanded state. Additionally stent 10 can be non-tapered or tapered in the expanded state.

Typically the guidewire 160 is inserted into the vein or artery and advanced to the target site. The catheter shaft 154 is then forwarded over the guidewire 160 to position the stent 10 and balloon 146 into position at the target site. Once in position the balloon 146 is inflated through the balloon channel 156 to expand the stent 10 from a crimped to an expanded state. In the expanded state, the stent 10 provides the desired scaffolding support to the vessel. Once the stent 10 has been expanded, the balloon 146 is deflated and the catheter shaft, 154, balloon 146, and guidewire 160 are withdrawn from the patient.

The stent of the present invention can be made as short as less than 10 mm in length or as long as 100 mm or more. If long stents are to be used, however, matching length or preferably slightly longer delivery catheter balloons will typically be needed to expand the stents into their deployed positions. Long stents, depending on the target vessel, may require curved long balloons, tapered long balloons or curved and tapered long balloons for deployment. Curved and/or tapered balloons which match the natural curve and taper of a blood vessel reduce stress on the blood vessel during and after stent deployment. This is especially important in many coronary applications which involve stenting in curved and tapered coronary vessels. The use of such curved and/or tapered balloons is within the scope of the present invention.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The invention claimed is:

1. A stent comprising a plurality of longitudinally adjacent columns, each column formed of a plurality of struts, the plurality of columns including first columns and second columns, each of the struts of at least one of the first columns having a first width, each of the struts of at least one of the second columns having a second width less than the first width, the struts of at least one of the first columns interconnected by turns, one second column engaging two adjacent first columns, the struts of the second column extending between a turn of one of the adjacent first columns and a turn of the other of the adjacent first columns, each strut of the second column having at least two bends, a first end, and a second end, the first end longitudinally and circumferentially displaced from the second end.

2. The stent of claim 1, each strut of at least one of the second columns being curvilinear.

3. The stent of claim 1, the turn of the one adjacent first column and the turn of the other adjacent first column facing opposite directions.

4. The stent of claim 1, each first column having a first longitudinal width and each second column having a second longitudinal width less than the first longitudinal width.

5. The stent of claim 1, wherein a ratio of struts of a first column to struts of a second column is two to one.

6. The stent of claim 1, wherein the two adjacent first columns and the second column engaging the two adjacent first columns define a plurality of asymmetrical cell spaces.

7. The stent of claim 1, wherein the turn of the one adjacent first column and the turn of the other adjacent first column are circumferentially displaced.

8. The stent of claim 1, each turn of at least one of the first columns connecting two struts, each of the turns forming a first angle with one of the two struts and a second angle with the other of the two struts, the second angle being greater than the first angle.

9. The stent of claim 8, wherein the first angle is less than ninety degrees and the second angle is greater than ninety degrees.

10. The stent of claim 1, wherein the struts of each first column are uniformly spaced apart.

11. The stent of claim 1, wherein the struts of at least one of the first columns are spaced to define loop slots, the loop slots including first loop slots with a first width and second loop slots with a second width greater than the first width.

12. The stent of claim 11, wherein the first and second loop slots alternate with one another.

\* \* \* \* \*